United States Patent
Zellmer et al.

(10) Patent No.: US 11,944,818 B2
(45) Date of Patent: Apr. 2, 2024

(54) SYSTEM AND METHOD FOR EMBEDDING ELECTRONIC COMPONENTS WITHIN AN IMPLANT

(71) Applicant: INTELLIGENT IMPLANTS LIMITED, Cork (IE)

(72) Inventors: Erik Robert Zellmer, Gothenburg (SE); Rory Kenneth John Murphy, Phoenix, AZ (US)

(73) Assignee: Intelligent Implants Limited, Cork (IE)

( * ) Notice: Subject to any disclaimer, the term of this patent is extended or adjusted under 35 U.S.C. 154(b) by 350 days.

(21) Appl. No.: 17/087,155

(22) Filed: Nov. 2, 2020

(65) Prior Publication Data
US 2021/0128919 A1    May 6, 2021

Related U.S. Application Data

(60) Provisional application No. 63/025,831, filed on May 15, 2020, provisional application No. 62/976,139, (Continued)

(51) Int. Cl.
*A61F 2/44* (2006.01)
*A61F 2/28* (2006.01)
(Continued)

(52) U.S. Cl.
CPC ............ *A61N 1/36125* (2013.01); *A61F 2/28* (2013.01); *A61N 1/0551* (2013.01); *A61N 1/326* (2013.01);
(Continued)

(58) Field of Classification Search
CPC ...... A61N 1/326; A61N 1/0551; A61N 1/375; A61N 1/3758; A61B 5/053; A61B 5/4504; A61B 5/4566; A61B 5/686
See application file for complete search history.

(56) References Cited

U.S. PATENT DOCUMENTS

| | | | |
|---|---|---|---|
| 3,842,841 | A | 10/1974 | Brighton et al. |
| 4,175,565 | A | 11/1979 | Chiarenza et al. |

(Continued)

FOREIGN PATENT DOCUMENTS

| | | |
|---|---|---|
| EP | 3789079 A1 | 3/2021 |
| WO | 2013188380 A1 | 12/2013 |
| WO | 2014089299 A3 | 10/2014 |

OTHER PUBLICATIONS

Aughner Ji, et al. (2013) A Fully Implantable Pacemaker for the Mouse: From Battery to Wireless Power. PLOS ONE 8(10): e76291. https://doi.org/10.1371/journal.pone.0076291, Oct. 23, 2013.

(Continued)

*Primary Examiner* — Eduardo C Robert
*Assistant Examiner* — Michelle C Eckman
(74) *Attorney, Agent, or Firm* — Alpine Patents LLC; Brian Van Osdol

(57) ABSTRACT

A system and method for embedded electronics within a medical implant comprising: an implant body; a circuitry surface, containing at least one electronic component, wherein the circuitry surface is at least partially embedded within a defined cavity of the implant along at least one path; sheathing, comprising a protective structure, wherein the at least partially embedded portion of the circuitry surface is enclosed within the sheathing; electronic components connected to, or directly on, the circuitry surface, comprising a set of electrodes and an antenna; and wiring, connecting the circuitry surface and electronic components. The system and method may further include a casing, wherein the casing is a sealed structure directly connected to the implant body including a printed a circuit board (PCB) contained within the casing itself.

15 Claims, 31 Drawing Sheets

Related U.S. Application Data filed on Feb. 13, 2020, provisional application No. 62/929,681, filed on Nov. 1, 2019.

(51) Int. Cl.
*A61N 1/05* (2006.01)
*A61N 1/32* (2006.01)
*A61N 1/36* (2006.01)
*A61N 1/375* (2006.01)

(52) U.S. Cl.
CPC ....... *A61N 1/36062* (2017.08); *A61N 1/3758* (2013.01); *A61F 2/442* (2013.01); *A61F 2/447* (2013.01)

(56) References Cited

U.S. PATENT DOCUMENTS

| | | | |
|---|---|---|---|
| 4,313,438 A | | 2/1982 | Greatbatch |
| 4,690,144 A | | 9/1987 | Rise et al. |
| 4,690,166 A | | 9/1987 | Howeth |
| 5,056,518 A | | 10/1991 | Pethica et al. |
| 5,330,477 A | * | 7/1994 | Crook .................... A61N 1/326 606/280 |
| 5,358,514 A | | 10/1994 | Schulman et al. |
| 5,441,527 A | | 8/1995 | Erickson et al. |
| 5,458,627 A | | 10/1995 | Baranowski, Jr. et al. |
| 5,565,005 A | | 10/1996 | Erickson et al. |
| 5,974,342 A | | 10/1999 | Petrofsky |
| 5,989,289 A | | 11/1999 | Coates et al. |
| 6,120,502 A | | 9/2000 | Michelson |
| 6,292,699 B1 | | 9/2001 | Simon et al. |
| 6,400,990 B1 | | 6/2002 | Silvian |
| 6,582,467 B1 | | 6/2003 | Teitelbaum et al. |
| 6,605,089 B1 | | 8/2003 | Michelson |
| 7,104,986 B2 | | 9/2006 | Hovda et al. |
| 7,309,338 B2 | | 12/2007 | Cragg |
| 7,324,852 B2 | | 1/2008 | Barolat et al. |
| 7,359,755 B2 | | 4/2008 | Jones et al. |
| 7,455,672 B2 | | 11/2008 | Michelson |
| 7,578,819 B2 | | 8/2009 | Bleich et al. |
| 7,935,116 B2 | | 5/2011 | Michelson |
| 8,014,873 B2 | | 9/2011 | Jones et al. |
| 8,078,282 B2 | | 12/2011 | Nycz |
| 8,078,283 B2 | | 12/2011 | Cowan et al. |
| 8,206,387 B2 | | 6/2012 | Michelson |
| 8,463,401 B2 | | 6/2013 | Jones et al. |
| 8,666,471 B2 | * | 3/2014 | Rogers ................. A61B 5/6867 607/116 |
| 8,718,777 B2 | | 5/2014 | Lowry et al. |
| 8,740,879 B2 | | 6/2014 | Martinson et al. |
| 8,771,360 B2 | | 7/2014 | Jimenez et al. |
| 8,838,249 B2 | | 9/2014 | Nycz |
| 8,903,502 B2 | | 12/2014 | Perryman et al. |
| 10,292,831 B2 | | 5/2019 | Zellmer et al. |
| 10,617,880 B2 | | 4/2020 | Zellmer et al. |
| 11,097,096 B2 | * | 8/2021 | Linden ................... A61N 1/05 |
| 2003/0078634 A1 | | 4/2003 | Schulman et al. |
| 2004/0249373 A1 | | 12/2004 | Gronemeyer et al. |
| 2005/0033393 A1 | | 2/2005 | Daglow |
| 2005/0216702 A1 | | 9/2005 | Paolucci et al. |
| 2007/0250045 A1 | | 10/2007 | Trieu |
| 2008/0039901 A1 | | 2/2008 | Kronberg et al. |
| 2008/0294211 A1 | | 11/2008 | Moffitt |
| 2008/0300660 A1 | | 12/2008 | John |
| 2009/0062886 A1 | | 3/2009 | O'Handley et al. |
| 2010/0168829 A1 | | 7/2010 | Schwartz et al. |
| 2010/0204551 A1 | | 8/2010 | Roche |
| 2010/0292756 A1 | | 11/2010 | Schneider |
| 2011/0009728 A1 | | 1/2011 | Schouenborg |
| 2011/0087315 A1 | | 4/2011 | Richardson-Burns et al. |
| 2011/0092948 A1 | | 4/2011 | Shachar et al. |
| 2011/0301716 A1 | | 12/2011 | Sirivisoot et al. |
| 2013/0150970 A1 | | 6/2013 | Thaiyananthan |
| 2013/0165991 A1 | | 6/2013 | Kim et al. |
| 2013/0296940 A1 | | 11/2013 | Northcutt et al. |
| 2014/0114382 A1 | | 4/2014 | Kim |
| 2014/0133123 A1 | | 5/2014 | Prasannakumar et al. |
| 2014/0275847 A1 | | 9/2014 | Perryman et al. |
| 2014/0277260 A1 | | 9/2014 | Khalil et al. |
| 2014/0371823 A1 | | 12/2014 | Mashiach et al. |
| 2015/0018728 A1 | | 1/2015 | Gross et al. |
| 2015/0134061 A1 | | 5/2015 | Friis et al. |
| 2015/0187320 A1 | | 7/2015 | Ren |
| 2016/0270927 A1 | | 9/2016 | Zellmer et al. |
| 2017/0007420 A1 | | 1/2017 | Stevenson et al. |
| 2017/0246448 A1 | | 8/2017 | Lenoble et al. |
| 2018/0078774 A1 | * | 3/2018 | Strommer .......... A61N 1/36125 |
| 2018/0208992 A1 | | 7/2018 | Langevin et al. |
| 2018/0310964 A1 | | 11/2018 | Stevenson et al. |
| 2019/0224022 A1 | | 7/2019 | Zellmer et al. |
| 2019/0247198 A1 | | 8/2019 | Zellmer et al. |
| 2020/0107940 A1 | * | 4/2020 | Murphy ................. A61N 1/378 |
| 2020/0108252 A1 | | 4/2020 | Zellmer et al. |
| 2020/0206516 A1 | | 7/2020 | Zellmer et al. |
| 2020/0297513 A1 | | 9/2020 | Zellmer et al. |
| 2020/0352723 A1 | * | 11/2020 | Jimenez ................ A61F 2/4611 |

OTHER PUBLICATIONS

WIPO European Searching Authority, "PCT2016000482 WO Search And Opinion", dated Jul. 7, 2016.

* cited by examiner

Constructing a circuit S110

Building an implant body around the circuit S120

FIGURE 24

Constructing a circuitry surface with a set of electronic components that comprises at least one conductively connected antenna and a conductively connected set of electrodes S1110

Configuring the circuitry surface along a path S1112

Molding an implant body around the circuitry surface S1120.

Obtaining a circuit S210

Obtaining an implant body S220

Manufacturing a defined circuit cavity in the implant body S230

Embedding the circuit within the implant body S240

FIGURE 27

SYSTEM AND METHOD FOR EMBEDDING ELECTRONIC COMPONENTS WITHIN AN IMPLANT

CROSS-REFERENCE TO RELATED APPLICATIONS

This Application claims the benefit of U.S. Provisional Application No. 62/929,681, filed on 1 Nov. 2019, and U.S. Provisional Application No. 62/976,139, filed on 13 Feb. 2020, and U.S. Provisional Application No. 63/025,831, which was filed on 15 May 2020, all of which are incorporated in their entireties by this reference.

TECHNICAL FIELD

This invention relates generally to the field of medical implants, and more specifically to a new and useful system and method of embedding electronic components within an implant.

BACKGROUND

Spinal fusion is one of the most commonly performed surgical procedures within the US and in Europe. The goal of spinal fusion surgery is to introduce bone growth between two or more vertebrae, fusing them into a single, continuous unit. Spinal fusion surgery is performed in the lumbar, cervical and thoracic regions, and fusions within each region are associated with a different set of complications. Even so, most complications following spinal fusion can be generalized into two broad categories: non-fusions, where the vertebrae are not fused into a singular unit due to insufficient bone formation within the fusion space; heterotopic ossification, where bone growth damages or impinges on tissue causing harm or discomfort to the patient. Examples of heterotopic ossification includes: Anterior osteophyte formation causing mass effect on the esophagus leading difficulty of swallowing (cervical fusions); ossification of the posterior longitudinal ligament; and formation of posterior osteophyte and/or other excessive posterior bone growth pressuring the spinal cord and/or spinal nerves.

Currently, some risk of non-unions may be reduced using implantable or external electrical stimulators. Many existing implantable stimulators use hermetically-sealed, constant-current DC power sources attached to one or more electrodes, which can be large, unwieldy and prone to infection or complications. In addition, the electrodes of these implantable systems are long and are liable to break. Since implantable systems are designed to be placed along the length of the spine covering multiple vertebrae, they often migrate and may cause injury.

As the technology and usage of spinal fusion hardware improve, and more generally, the technology and usage of long-term implants improve, a greater emphasis needs to be placed on placement and preservation of electronic components of the implant. With improving technologies, electronic components play a greater role in the effectiveness of the implant but are often the most susceptible to deterioration over time within the body and may additionally cause the most harm to the body once they start breaking down. Furthermore, many of the materials and manufacturing techniques previously available suffer from incompatibility with electronics. For example, manufacturing temperatures for some materials would destroy adjacent electronics. Thus, there is a need in the medical implant field to create a new and useful system and method for embedding electronic components within an implant. This invention provides such a new and useful system and method.

BRIEF DESCRIPTION OF THE FIGURES

FIG. 24 is a flowchart of a first method of a preferred embodiment.

FIG. 27 is a flowchart of a second method of a preferred embodiment.

DESCRIPTION OF THE EMBODIMENTS

The following description of the embodiments of the invention is not intended to limit the invention to these embodiments but rather to enable a person skilled in the art to make and use this invention.

1. Overview

A system and method for embedding electronic components within an implant body functions to address manufacturing challenges in efficiently and robustly integrating electronics in medical device implants. In particular, the system and method address embedding electronic components in orthopedic implants, more specifically, spinal cage implants (also known as intervertebral body fusion device) used for spinal fusion operations.

The system and method enable a medical implant device with internally integrated electronics (e.g., an orthopedic implant such as a spinal cage) and/or enable the building of such a medical implant. More specifically, the system and method may provide for a spinal implant with a set of electrodes, to stimulate and/or monitor bone growth, and an antenna for control and powering of the electrodes. The set of electrodes may be internally integrated so that discrete electrode sites are exposed on the surface of the implant. The one or more antennas can be internally embedded and used for energy coupling (e.g., for wireless charging/powering) and/or wireless communication. In some variations, the system and method enable a medical implant with antennas at different orientations.

Figure 1:
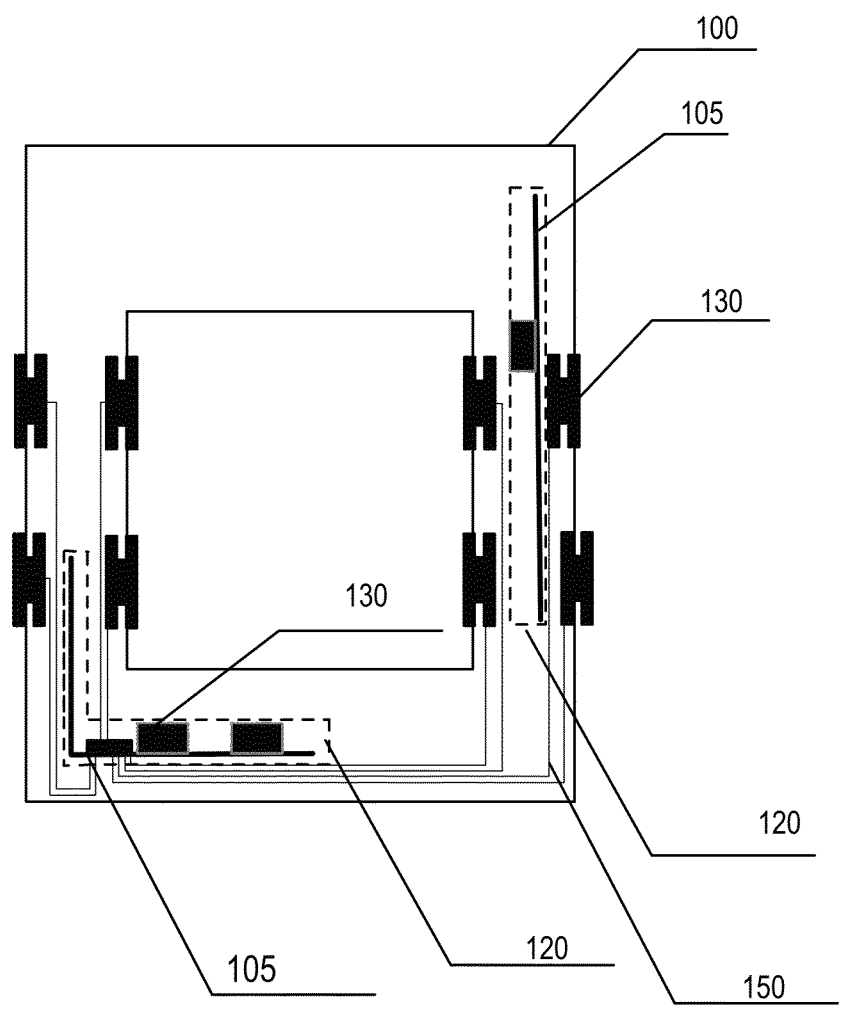
FIG. 1 is a schematic representation of a variation of the system.

As shown in FIG. 1, a system and method include: an implant body and a circuitry system that includes at least one circuitry surface that is integrated with at least one functional electronic component; wherein the circuitry surface is integrated within the implant body. In particular, the implant body is made of a biocompatible implant material such as polyether ether ketone (PEEK). The at least one functional electronic component of the circuitry surface can include one or more electrodes and/or an antenna. The circuitry surface is preferably embedded, at least partially, within the implant body in a specific geometry so as to fit within the form of the implant body and also to potentially properly position and distribute different electronic components like electrodes and antennas to specific locations in the implant. This geometry within the implant body is defined as an internal cavity of the implant body to contain the circuitry surface along at least one path. The path of the circuitry surface through the implant body may be a line, curve, and/or connected path segments. Thus, the circuitry surface embedded along a single path may have a line or curve geometry. The circuitry surface embedded in the implant body along a plurality of paths may then have a geometry that includes folds, bends, table-like, and/or more complex geometries. The system and method may further include a sheathing (e.g., coating and/or structural members) along the circuitry surface for protection and/or support.

The system and method may anticipate many challenges in incorporating electrical components into a biocompatible medical implant. It may also anticipate challenges of incorporating electrical components into load-bearing medical devices, for example a spinal cage, without compromising the mechanical properties of the medical device.

As a first example, the medical implant of the system and method can integrate electrical stimulation features, wireless charging/communication/powering, and/or other electronics-enabled features with minimal impact to size of the overall implant. The system and method can allow for a biocompatible material such as PEEK to be injection molded, 3D printed, or otherwise formed around the circuitry surface.

As another example, the medical implant of the system and method can have integrated electronics internally embedded within biocompatible material like PEEK. Peek has a relatively high melting temperature which traditionally presents challenges for injection molding in proximity to active electronic components.

The circuitry surface comprises a roughly two-dimensional surface that may vary in shape and composition dependent on implementation. The circuitry surface functions as an embedded circuitry element (i.e., a "circuitry insert") integrated within an implant body material (e.g., an injection molded thermoplastic) The circuitry surface is a structural member that will, in many variations, have a substantially planar aspect ratio that can be embedded within an implant body to support integration of electrodes and antennas in their desired position. That is, the circuitry surface may comprise a relatively thin planar surface. Examples of circuitry surfaces included a printed circuit board (PCB) or another circuit system integrated with some physical scaffold, structure or substrate. In some variations, the system and method may further include multiple circuitry surfaces, wherein each circuitry surface is embedded, at least partially, within the implant body in a specific geometry. The system and method function as a system comprising an implant body with partially embedded circuitry system in a specific geometry, and a method to manufacture the system.

In some variations, the system and method may additionally include a casing, wherein the casing may contain one or more circuit systems that operatively connect to one or more circuitry surfaces. This variation may be used to integrate electronic components like antennas and/or electrodes within an implant body but then to have other portions of the whole circuit system contained within the casing. This casing may serve to mechanically and hermetically seal contained circuit system components, thereby protecting them from mechanical stress and bodily fluids. To serve this function, the casing may be produced using a different material than the rest of the rest of the implant body (for example a titanium casing with a PEEK implant body or vice versa). The casing may be completely or partially embedded and/or integrated with the implant body, serving as an inseparable subcomponent. The casing may alternatively be partially embedded and integrated such that it is detachable. In one exemplary variation, the casing electrically couples with the circuitry surfaces within the implant body through an electrical connector. The casing may then be welded, adhered, or otherwise at least semi-permanently attached to the implant body. The casing may provide a separation between the main implant body and internally contained PCB components. Such a casing may be produced in a separate process than the rest of the implant body, with the two geometries being joined/attached/adhered after each having been produced in separate processes. Alternatively, the casing and the rest of the implant body may be produced in inseparable steps, such as overmolding the implant body onto the casing, or 3D printing the casing onto the rest of the implant body.

The system and method may be applied to any implant that contains electronic components. As mentioned, the system and method may in particular provide benefits for devices that incorporate antennas and/or electrodes within an implant body. Herein, the system and method are primarily described as they apply to an orthopedic implant, and more specifically a spinal cage. In particular, the system and method may be used with a spinal cage implant with integrated electronics and containing exposed electrodes utilized to stimulate bone growth for damaged vertebrae and/or to sense bone growth. But the system and method are not limited to orthopedic implants and can be implemented generally for any polymer/metal implant construct that requires electronic components that can be implemented within a circuit system.

One potential benefit of the system and method is enhanced integration of electronics with biocompatible materials used for an implant body such as PEEK, other organic thermoplastic polymers in the polyaryletherketone (PAEK) family, and/or other materials, especially those that are manufactured using thermal material manipulation like injection molding or 3D printing. The system and method address manufacturing feasibility of incorporating temperature-sensitive electronics in a physical casing that uses manufacturing techniques depending on high temperatures. The process of manufacturing and the physical design of the system can address such feasibility risks.

An additional potential benefit of the system and method is reducing the minimum size of the implant. Embedding electronic components within an implant body reduces the space taken up by the electronic components as compared to, for example, if they were placed or attached outside the volume/external surfaces of the implant body, thereby enabling construction of an implant that is smaller than what was previously possible. Reducing the minimum size of the implant may simplify the implanting of the implant. Additionally, an even smaller implant may increase utilization of the implant in regions where, prior to this invention, such implants were considered too large. In a related potential, the number and size of electronic components may be greater than previously achieved as a result of the enhanced efficiency of integration.

Another potential benefit of embedding electronic components within an implant body is that the implant body may protect electronic components from corrosion. A major reason for implant failure is corrosion of the implant components within the human body. Non-reactive polymer components tend to be fairly resistant to corrosion but other components, particularly electronic components are not as resistant. Embedding electronics within the implant body may thus provide significant protection to the electronic components. This may overall increase the lifespan and effectiveness of the implant.

Another potential benefit of embedding electronic components is that the system and method may enable utilization of more "sensitive" electronic components that would deteriorate relatively quickly in the human body. Electronic components that were previously deemed too sensitive to corrosion, may be utilized with less worry of implant failure.

Along the same lines, another potential benefit of the system and method would be enabling utilization of electronic components that may be considered toxic to the human body. Electronic components embedded in the implant would also isolate the toxic electronic component from the body and prevent harm that they may typically cause inside a living organism. In some events, the system and method can additionally act to physically restrict non-biocompatible materials from being exposed to the body in the event of failure or during removal of the implant. Some variations of the system and method can be used in sealing or encasing particular elements to prevent exposure of the body to various materials of a circuitry system. This protection can be critical during surgery, during use of the medical implant within the body, and/or during extraction of the medical implant.

Another potential benefit of the system and method is maximizing the effectiveness of some electronic components with respect to the implant body. By embedding a circuitry surface within the implant body with a specific geometry, positioning of specific electronic components may be optimized for functionality. The specific geometry may enable positioning of components for maximum effect (e.g. sensors on a surface of the implant, control systems deep inside, electrodes in specific locations on the surface, antennas wrapped around the circuitry surface to provide optimal signal transfer).

A potential benefit of the system and method that includes an attachment casing is the ease of incorporation of a circuit system as part of the implant. Some preferred implementations of the casing provide a simple and durable structure to house a circuit system including elements like a PCB and other electronic components. In some variations, the casing may then be incorporated with implant body as a single structure, thereby providing PCB incorporation without any modifications to the implant body.

Another potential benefit of the system and method that include an attachment casing, is that the casing may provide an easy and robust enclosure for at least a portion of the electronic components of a circuit system. In preferred variations, the casing may be constructed such that it is resistant to the high levels of stress and strain within a patient's body (e.g. constructed of titanium) as well as the high levels of stress and strain experienced during implantation, for example during impacting of a spinal cage. By incorporating electronic components within the casing, they may thus be protected from these mechanical stresses.

Another potential benefit of the system and method is the use of implementing an electronics-enabled medical implant device that secures potentially bio-incompatible circuitry components within the casing. Furthermore, the casing may potentially provide the particular benefit of being more resistant to levels of stress and strain within a patient's body as compared to the rest of the medical implant. The casing may be made of mechanically robust material like Titanium, which can make the casing highly resistant to stress and strain despite a potentially defined inner chamber to accommodate the housing of a portion of the circuitry system. Thus, electronics in the casing may remain sealed in the unlikely event that the rest of the medical implant fails mechanically or if the medical implant device breaks during removal and/or implantation. In this way, the system and method can enable a medical implant device where potentially toxic/non-biocompatible circuit components (e.g., integrated circuits, capacitors, resistors, and other circuit components) can be secured within the casing with ideally less chance of exposure to the body, while electrodes, an antenna, and/or other electronics that may be located in the implant body can be made from biocompatible materials like titanium, gold, platinum-iridium, polyamide, and/or medical grade silicone.

Preferably, electronic components are hermetically sealed within the attachment casing, completely isolating electronic components from bodily fluids. Bodily fluids may cause damage and/or deterioration to electronic components. Additionally, some electronic components may be toxic to a patient. Hermetically sealing electronic components in the casing may thus provide the benefit of protection to the patient from electronic toxic components, and additionally protect electronic components from damage or deterioration.

Another potential benefit of the system and method that include an attachment casing, is that the attachment casing enables access and removal of at least a portion of the circuitry system without disturbing the main implant body. For implant utilization, the attachment casing may be modified, to change PCB circuitry with minimal effect on the implant body.

Additionally, for long term implant utilization, the attachment casing may provide the added benefit of easy removal of potentially toxic PCB components. Once the system and method has finished "active" functionality that requires PCB utilization, the implant may sit in patient's body for years and decades. During this time, implant deterioration may lead to PCB exposure, and potentially exposure to toxic components on the PCB. Removal of the attachment casing may add the potential benefit of simpler removal of these toxic components while leaving the main implant body in place, undisturbed.

2. System

Figure 2:
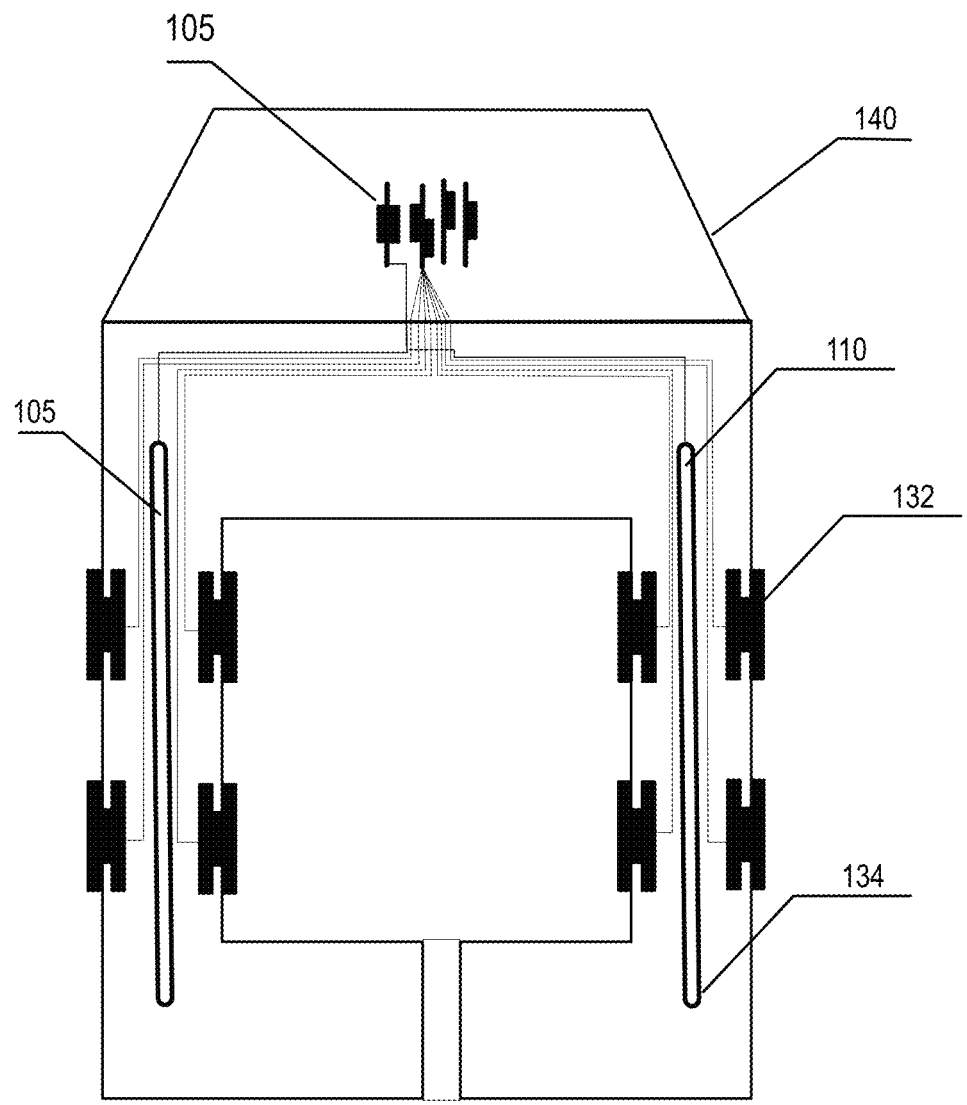
FIG. 2 is a schematic representation of another variation of the system.

As shown in FIGS. 1 and 2, a system for embedded electronics within a medical implant includes: an implant body 100; a circuitry system 105, containing at least one electronic component; electronic components 130 connected to, or directly on the circuitry system, comprising a set of electrodes 132 and an antenna 134; and wiring 150, connecting the circuitry system and electronic components. In some variations, the circuitry system comprises at least one circuitry surface 110, containing the at least one electronic component, wherein the circuitry surface is at least partially embedded within a defined cavity of the implant body along at least one path. In some variations, the system can additionally include sheathing 120, comprising a protective structure, wherein an at least partially embedded portion of the circuitry system 105 is enclosed within the sheathing.

Variations of the path of the defined cavity may include a straight channel, a channel of a uniform profile, a curved channel, an angled channel, and/or other variations as described herein. The system functions as an implant with functional circuitry, wherein the circuitry is additionally protected by the implant body 100, and for the most part, takes up little additional space beyond the implant body itself. The system may particularly have functionality as a structural implant that can provide electrical stimulation. Examples of possible system implementations include: orthopedic cages (e.g. spine cages), pacemakers, and surgical nails. Dependent on system implementation, the system may comprise fewer components, or include additional components as desired.

As shown in FIG. 2, in some variations, the system may further include a casing 140, wherein the casing is a sealed structure directly connected to the implant body 100. In variations with a casing 140, the circuitry system 105 includes a casing circuitry subsystem (e.g., a printed circuit board (PCB)) contained within the casing 140. Dependent on the implementation, the casing circuitry subsystem may include exposed electrical connectors or couplers that operatively connect to one or more circuitry surfaces no within the implant body 100. The casing 140 variation of the system may function to provide different benefits to manufacturability as well as an alternative approach to sealing and protecting some types of electronic components 130 like active electronics, integrated circuits, and/or other sensitive components. In some variations, the casing circuitry subsystem can include all circuitry components that pose biocompatibility risk, which can be sealed or otherwise contained in the casing 140.

The implant body 100 of a preferred embodiment may have any general function as desired or required for a particular implementation. In one preferred variation, the implant body 100 may be any non-biological implant that may be implanted into a living organism (e.g. spinal cage, pacemaker, nail). Dependent on implementation, as a component of the system, the implant body 100 may function as a three-dimensional housing structure that contains at least one circuitry surface 110. In some variations, the implant body 100 is made as a load-bearing structure that is subjected to stress and forces during implantation in a body such as with the implant body of a spinal cage, nail, hip implant, and the like. The implant body 100 is preferably of a geometry larger than the circuitry surface 110 and constructed of a solid, non-reactive, non-toxic, and/or malleable material. Additional or alternative material attributes may also be used for the material of the implant body 100.

In preferred variations, the implant body 100 may be the implant component such as the one described in U.S. patent application Ser. No. 15/075,152 filed on 19 Mar. 2016, which is hereby incorporated in its entirety. The implant body 100 may alternatively be an orthopedic implant distinct from the one in U.S. application Ser. No. 15/075,152. The implant body 100 may function as the structural element housing, or holding, implant subcomponents. In some variations, the implant body 100 is flexible, but the implant body may alternatively be semi-flexible or rigid.

Figure 3:
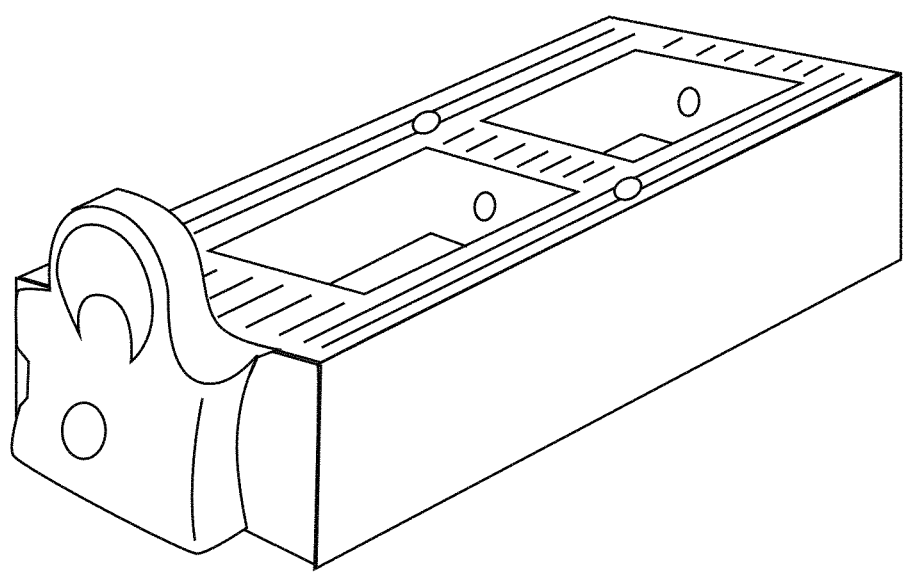
FIGS. 3-5 are schematic representations of exemplary spinal cage implants.

The implant body 100 is preferably made of non-conductive material but may be partially conductive. In some embodiments, the implant body 100 can be a spinal implant, more preferably a spinal cage. The implant body 100 is preferably composed of a non-conductive polymer, such as polyether ether ketone (PEEK); but may be made of engineered, natural, or synthetic bone material; titanium; and/or other suitable material(s) or combinations thereof. In some implementations, the implant body 100 may have additional components of different construction, such as a metal end on the spinal cage (e.g. as shown in FIG. 3).

Figure 4:
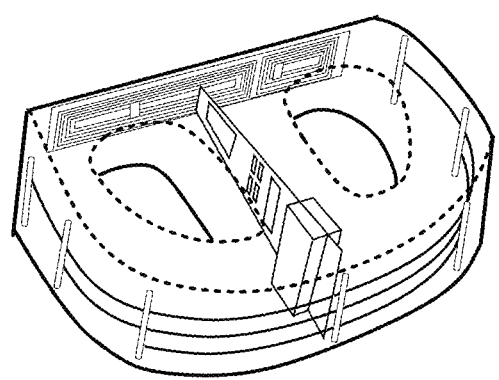
Figure 5:
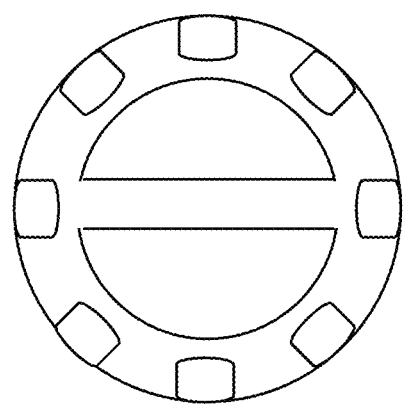

In some preferred variations, the implant body 100 is a spinal cage. Alternatively, the implant body 100 may be another type of orthopedic implant, or other type of implant body (e.g. pacemaker). In some implementations, the spinal cage geometry is an extruded prism of some defined form, which generally has a continuous outline. The spinal cage can include one or more graft windows, which can be defined as internal implant cavities. That is, the spinal cage may include wall enclosures on the lateral sides of the implant body 100, potentially defining one or more implant cavities; with openings on the top and bottom surface of the spinal cage. As shown in the example sketches of FIGS. 3-5, the spinal cage may include the aforementioned description and still may be incorporated with many geometries. Examples of specific types/shapes of spinal cages that may be implemented include, but are not limited to: anterior lumbar interbody fusion (ALIF) cages, transforaminal lumbar interbody fusion (TLIF) cages, eXtreme lateral interbody fusion (XLIF) cages, posterior lumbar interbody fusion (PLIF) cages, anterior cervical fusion (ACF) cages, lateral cages, oblique lateral interbody fusion cages (OLIF) and/or other suitable types of spinal cages. The spinal cage may additionally include other design features such as: surface coatings (e.g. to protect the implant, increase osteointegration, etc.), surgery tool attachment points (e.g. for easier tool utilization), teeth (e.g. to increase the chance that the spinal cage does not move), lateral openings in the spinal cage (e.g. to enable electric charge to more easily enter or exit the spinal cage and/or other elements).

Figure 6:
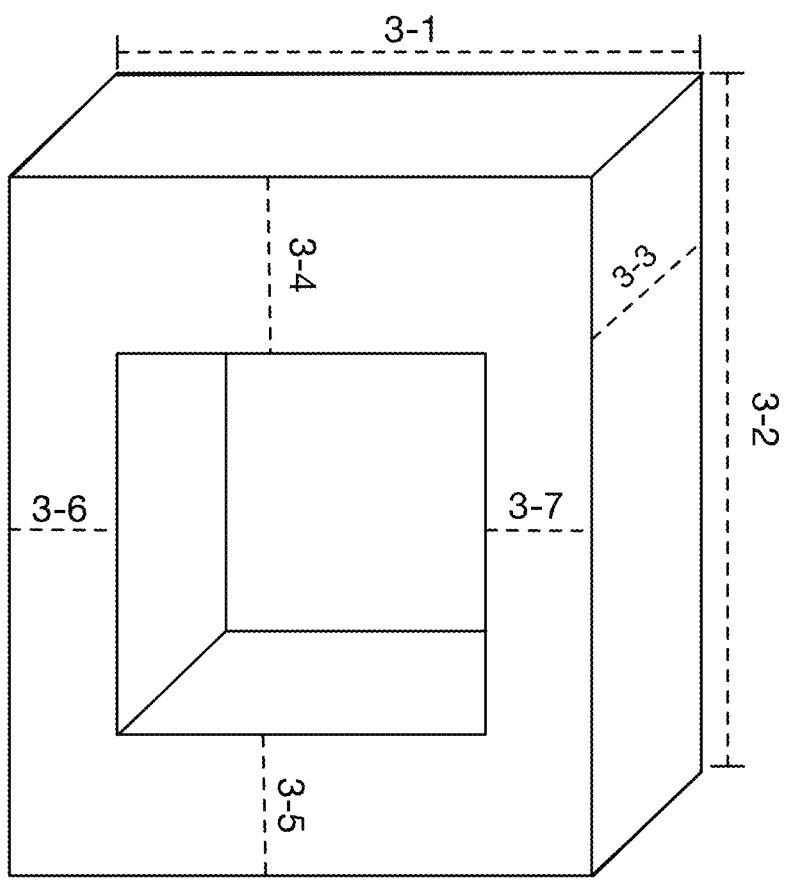
FIG. 6 is a schematic representation of a spinal cage showing exemplary dimensions.

In addition to different geometries, the spinal cage may have different sizes as desired or required for implementation. As the spinal cage is implanted into the spinal column to replace damaged disk/bone tissue, the size (and shape) of the implant body 100 may be varied to fit, to enable and optimize appropriate function in the damaged tissue region. As shown in FIG. 6, one variation of the implant body geometry can be a spinal cage with a single implant cavity, wherein the side of the implant body 100 facing outward is the top of the implant body as oriented in a human patient. Typical dimensions for some preferred implementations, such as shown in FIG. 6, may range from: 3-1=9 mm-50 mm, 3-2=20 mm-80 mm, 3-3=5 mm-18 mm, 3-4=5-30 mm, 3-5=5-30 mm, 3-6=1 mm-5 mm, 3-7=1 mm-5 mm. Although these are typical ranges, actual implementations may vary beyond these ranges if desired.

The system preferably includes a circuitry system 105 which may include one, or multiple, circuitry surfaces 110. The circuitry system 105 may include any electrical component, connector, or functional component of a circuit system. In one variation, the circuitry system 105 may be implemented fully through a circuitry surface 110 embedded within an implant body 100. In another variation, the circuitry system 105 may include a casing circuitry subsystem, wherein the casing circuitry subsystem is a portion of the circuitry system that is embedded within a casing 140. The casing circuitry subsystem can be connected to one or more circuitry surfaces 110. The casing-embedded circuitry system can be connected to a circuitry surface 110 through wiring 150, i.e. a wired conductive connection. The casing-embedded circuitry system may alternatively, in some variations, be operatively connected using inductive coupling or other wireless coupling systems.

The circuitry surface 110 of a preferred embodiment functions as a roughly two-dimensional surface (e.g. flat plane, bended plane, curved plane, hollow tube), for some and/or all electronic components 130 of the medical implant, wherein the circuitry surface 110 is at least partially embedded within the implant body 100. In some variations, at least a substantial portion of the circuitry surface 110 (e.g., greater than 95% of surface area of the circuitry surface 110) is embedded within the implant body. In one implementation, the implant body 100 is overmolded or otherwise formed around the circuitry surface 110 so as to cover a substantial portion. Portions of the circuitry surface 110 may be exposed in some variations. More specifically, electrodes 132 integrated with or otherwise connected to a circuitry surface 110 may be exposed. As a first example, exposed surfaces of electrodes 132 may be exposed at designated areas where electrical stimulation or electrical measurements are made. Similarly, electrical connectors, which are conductively coupled to the circuitry system subsystems of the circuitry surface 110 (e.g., electrodes 132 and/or antennas 134), may be exposed (i.e., not covered by the implant body 100) in particular sites.

As used herein, circuitry surface 110 may refer to a single, or plurality, of circuitry surfaces contained within the system with no loss of generality.

Preferably, the circuitry surface 110 is used in part as a scaffold or structure for orienting and facilitating integration of electronic components 130 into the implant body 100. In particular, the circuitry surface 110 is used to facilitate embedding and positioning electrical components 130 within the implant body 100 that have performance/operational properties dependent on orientation and positioning relative to the implant body 100. In particular, the position and orientation of one or more electrodes 132 and/or one or more antennas 134 may be formed within a manufactured implant body through attachment to the circuitry surface 110.

The position and relative orientation of electrodes 132 may be important such as in the case of a medical implant device capable of delivering electrical stimulation and/or making electrical measurements through the use of different combinations of electrodes. The circuitry surface 110 can facilitate orienting electrodes along different surface faces of the external body of an implant body 100. In many cases, the circuitry surface 110 is used to seamlessly integrate a plurality of electrodes (e.g., 4, 8, or more, electrodes) at different positions on external surfaces that are on at least two or more different defined faces and/or planes of the implant body 100. For example, electrodes 132 may be positioned, through physically coupling to the circuitry surface 110, along one of: an internal wall or walls defining an internal cavity (e.g., a defined bone fusion cavity in a spinal cage) and/or one or more external walls along an outer surface of the implant body 100.

The position and relative orientation of one or more antennas 134 may similarly be managed in a medical implant device through the structural scaffolding of the circuitry surface 110. Antenna positioning can be important to optimizing wireless power transfer and/or communication between the medical implant device and an external system. In some variations, antennas 134 may be oriented along different defined planes by being formed into or around a circuitry surface 110 and how that circuitry surface 110 is configured (e.g., folded) within the implant body 100.

Figure 7:
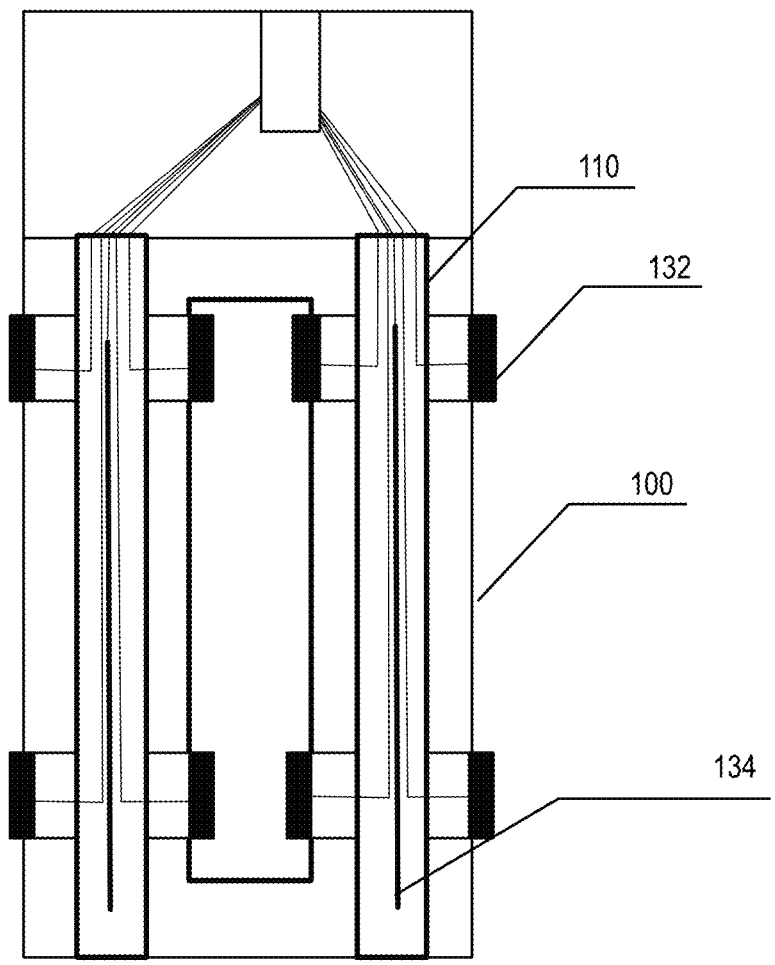
FIG. 7 is a cross-sectional schematic representation of a spinal cage.

The circuitry surface 110 may comprise any general, or specific, circuitry to enable the functionality of system electronic components 130. In one variation, the circuitry surface 110 may include a printed circuit board (PCB), wherein electronic components 130 are based on or connected to the PCB. In another variation, the circuitry surface 110 may include an integrated chip (IC), wherein electronic components 130 are built onto, or connected to the IC. For example, the circuitry surface 110 may include an application specific integrated chip (ASIC), wherein antenna 134 and capacitor components are built into the chip. In a third variation, the circuitry surface 110 may include cavity tube, wherein electronic components 130 are embedded within the tube, or wrapped around the tube (e.g. the antenna 134), as shown in FIGS. 2 and 7. In another variation, the circuitry surface 110 may contain biocompatible electronic components 130 such as one or more electrodes 132 and/or one or more antennas 134 which are connected through wiring 150 or other conductive coupler to another portion of the circuitry system 105 such as a casing circuitry subsystem.

The geometry of the embedded circuitry surface 110 within the implant body 100 may be simple, along a straight line (straight path) or a curved line (curved path). Alternatively, the geometry of the embedded circuitry surface 110 maybe more complex, comprising of multiple straight paths and/or curved paths. Utilizing multiple straight paths and/or complex paths, the geometries of the embedded circuitry surface 110 may contain any combination of folds, bends, and table geometries. These simple, and/or complex folds and paths may be dependent on the type of circuitry surface 110 (e.g. IC, PCB, orientation surface, etc.) and the potential space for implementation of a defined cavity geometry within the implant body 100.

Figure 8:
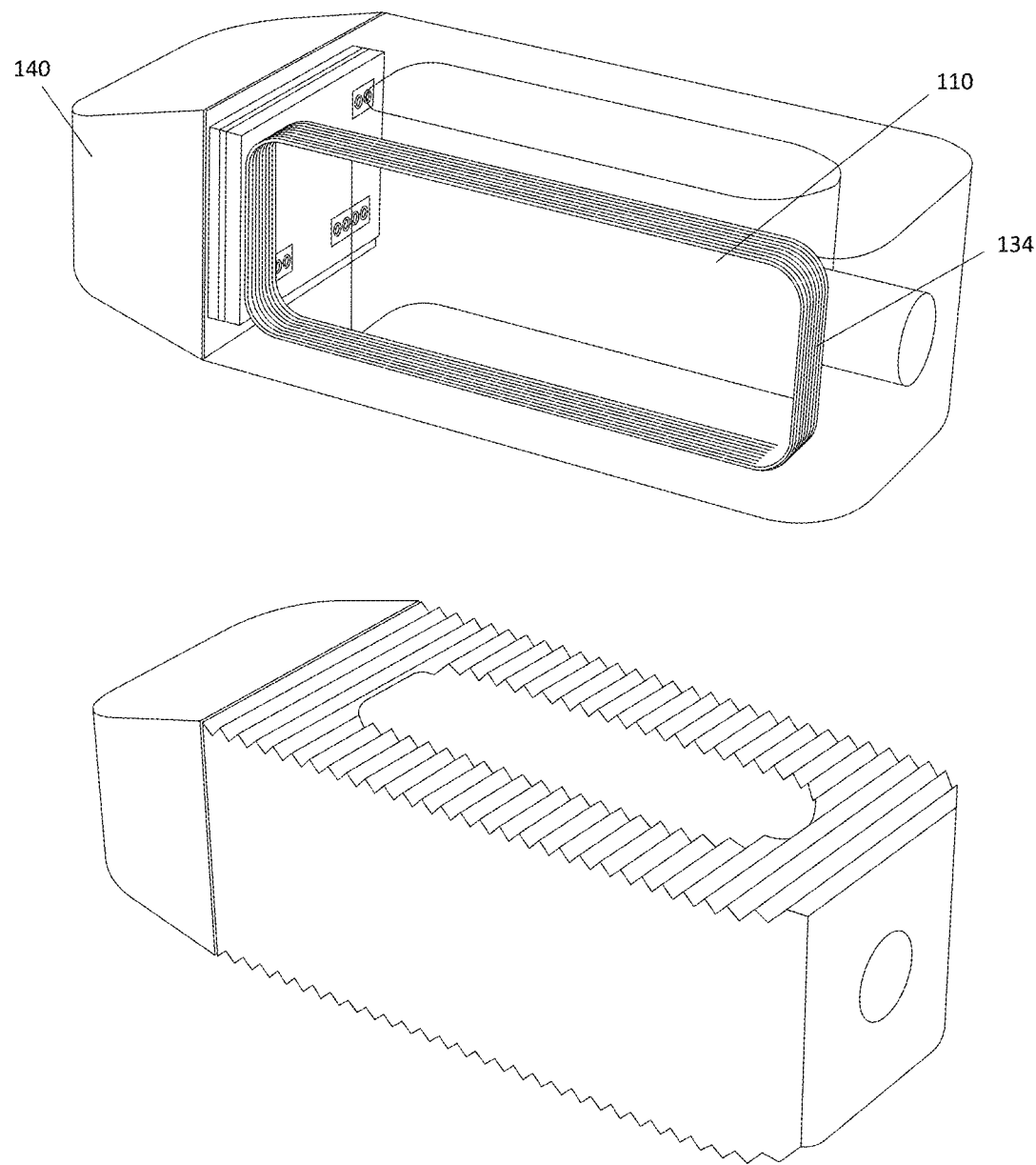
FIG. 8 is an illustration of a system first showing internal components including an antenna within an implant body (not shown) and then showing the implant body.
Figure 9:
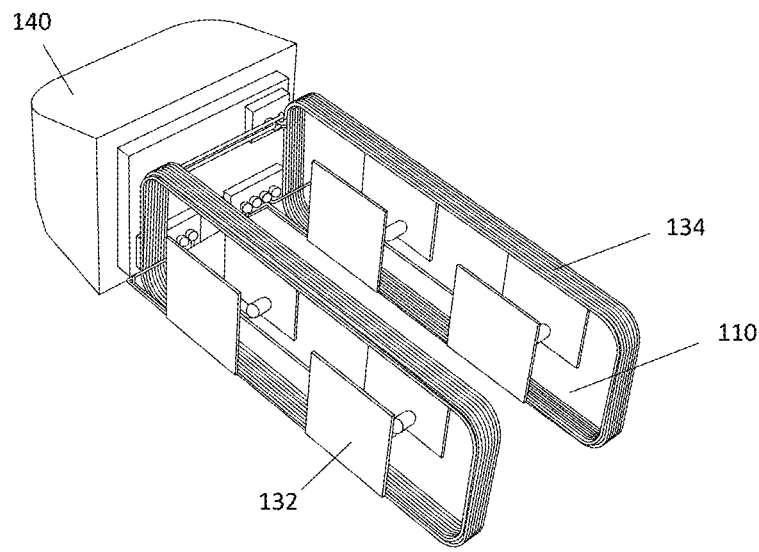
FIG. 9 is an illustration of a system first showing internal components including two antennas and eight electrodes that are within an implant body (not shown) and then showing the system with the implant body.
Figure 9:
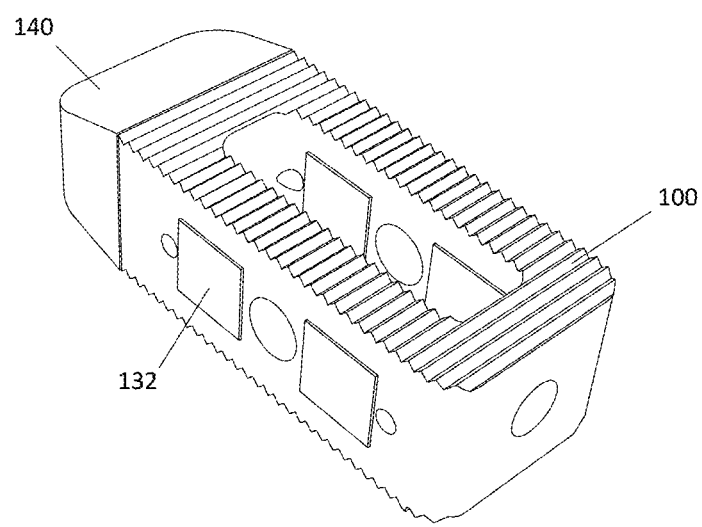

In some variations, the circuitry surface 110 comprises an orientation circuitry surface that functions as a structural frame such that other electronic components 130 may be mounted on and around. In these variations, electronic components 130 may be embedded or housed directly in the implant body 100 without a chip or circuit board. The circuitry surface 110 may still function to provide a fixed and orientable surface (e.g. for electrode positioning and antenna placement to wrap around. This may be the case for components that may be particularly resistant during implant construction (e.g. resistant to exposure from high temperatures). FIG. 8 and FIG. 9 both show renderings of an orientation circuitry surface 110, wherein enclosed are antennas 134 wrapped around the circuitry surface 110 (as shown in FIG. 8) and electrodes 132 oriented and connected through the circuitry surface (as shown in FIG. 9).

Figure 10:
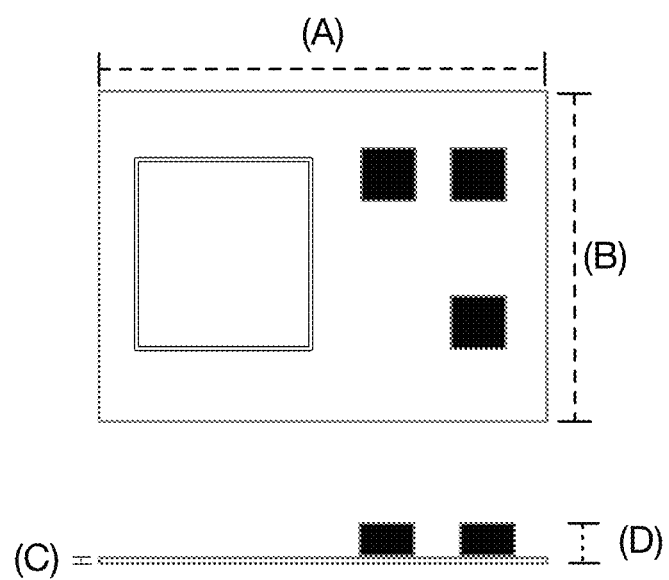
FIG. 10 is schematic representation of a printed circuit board (PCB) of a preferred embodiment.
Figure 11:
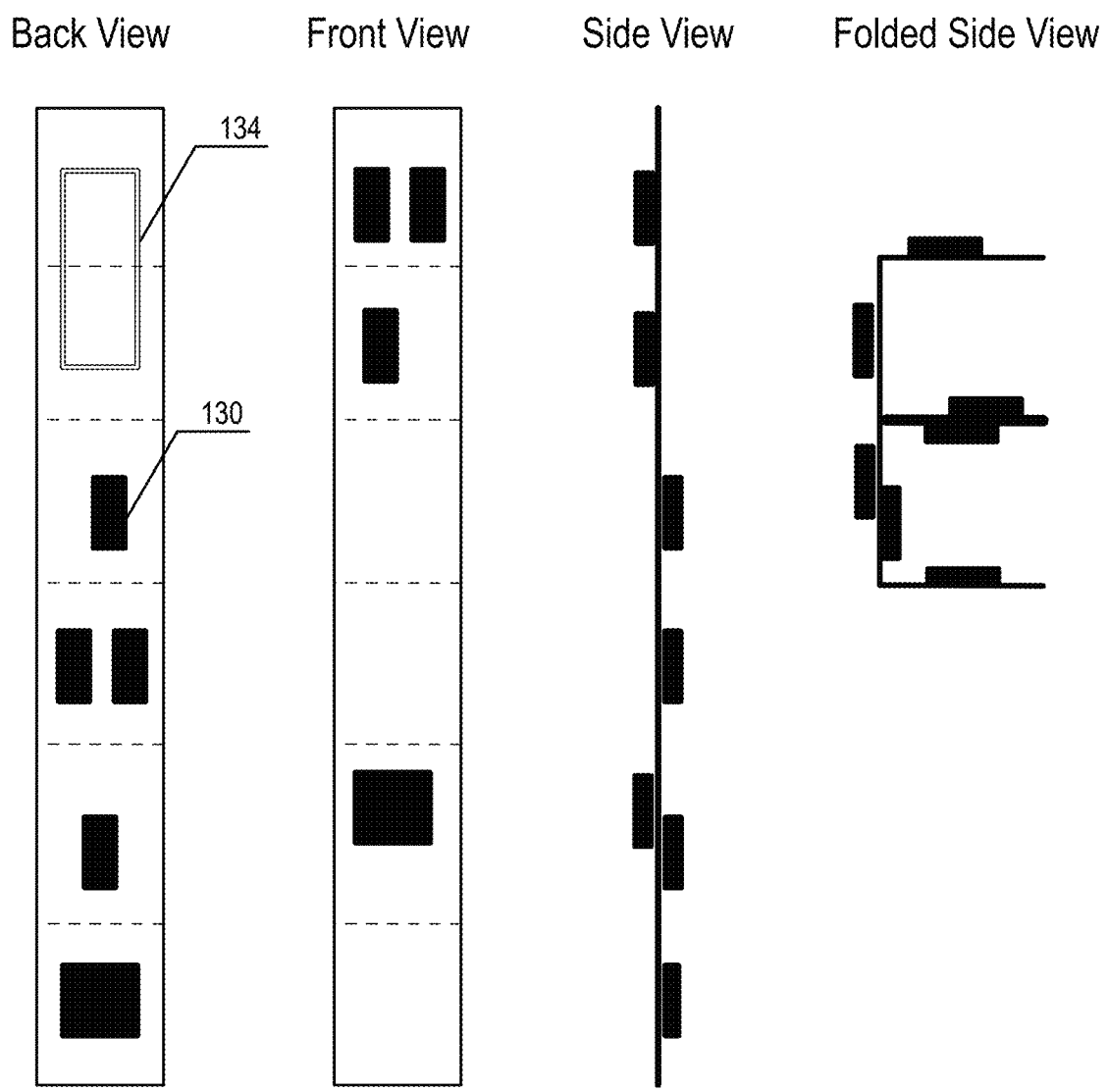
FIG. 11 is a schematic representation of different views of a PCB with component placement configured for complex folding arrangement shown in the Folded Side View.

In some variations, the circuitry surface 110 comprises at least one PCB as shown in FIG. 10; a schematic drawing of a single layer PCB from a front view (top) and side view (bottom). The PCB can be single-sided, double-sided, and/or multi-layered, wherein each side/layer may contain electronic components 130 embedded in, or on, the surface of the PCB. In some implementations, the PCB is single sided and single layered. In other implementations, the PCB may be multi-sided as shown in FIG. 11; A schematic drawing of a multi-sided PCB from a front view, back view, side view, and folded view. In preferred variations, the PCB itself may be flexible, wherein all or parts of the PCB are bendable (although electronic components 130 on the PCB may not be bendable). In other words, the PCB includes a flexible substrate. As the PCB is preferably part of a medical implant, the PCB may be constructed of any appropriate non-toxic non-reactive material. In preferable variations the PCB is constructed of polyimide, although other non-toxic, non-reactive materials may be alternatively used.

The PCB typically has a flat sheet-like geometry, wherein the size of the sheet (or layers of sheets) depends on the required activity desired from the PCB and physical space available for placement of the PCB. The PCB in one variation may be formed on a substrate with a rectangular shape profile. However, the PCB may alternatively be formed on a substrate with or modified to have a non-rectangular shape profile. For example, the PCB may have central rectangular region but with one or more sub-regions extending off the central rectangular region. In preferred variations, as shown in FIG. 10, the thickness of the PCB sheet is (C)=~0.1 mm. For the spinal cage variation, the PCB dimensions may vary depending on the specific implementation. In reference to FIG. 10, the dimensions of the PCB may typically range from (A)=10 mm-100 mm for the length, and (B)=1 mm-100 mm. In addition to the PCB thickness per se (C), electronic components 130 housed on the PCB may jut off the plane of the PCT and/or extend outward in some dimension, increasing the PCB thickness. For the spinal cage variation, (D)<5 mm while for some preferred implementations, (D)<=3 mm. For example, some PCB sheets (with components) have an effective thickness less than 1 mm such as having a thickness of approximately 0.6 mm. However, the implant body 100 may accommodate greater thicknesses in the event that the PCB is a flexible PCB and is folded, or layered, resulting in a thickness greater than the effective thickness of the PCB when flat.

The PCB may include bends and/or folds (although the general dimensions for the unbent/unfolded PCB described above may still hold). The PCB may include any number of bends and/or folds limited such that the final PCB geometry can be incorporated into the implant body 100 and that electronic components 130 on the PCB do not lose functionality (e.g. if the electronic component is situated on a PCB bend such that the electronic component is bent beyond function). In some variations, the PCB may layout components and leads in coordination with planned folding patterns. For example, electronic components 130 may be positioned outside a defined folding seam to facilitate easier folding. With respect to the topology of the electronic components 130 on the PCB, bends or folds may not occur on electronic components 130 that cannot be bent or folded. For example, an antenna region may be folded without affecting the functionality of the antenna 134, while a fold may damage the functionality of a capacitor, although a bend may have no effect on the functionality of the capacitor (depending on the angle of the bend). Preferably, the layout of the electronic components 130 on the PCB may be configured into defined regions. In particular, the layout of components may include flex regions with no or minimal electronic components or components compatible with flexing. For example, in a variation where the PCB includes a 90° angle bend, there may be a region with no electronic component 130 placement at the point of bending, and/or overlapping the region of bending/flexing. Additionally, conductive traces may be oriented across defined folding seams to mitigate mechanical issues of the leads.

Figure 12A:
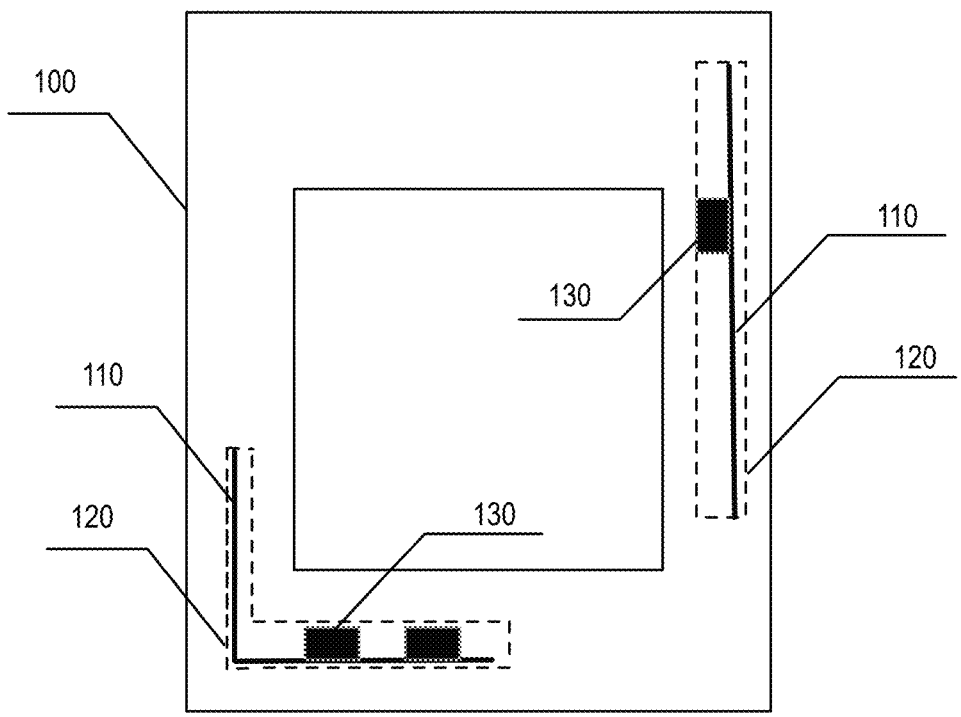
FIG. 12A is a schematic representation of a system variation with defined PCB cavity having a uniform profile.
Figure 12B:
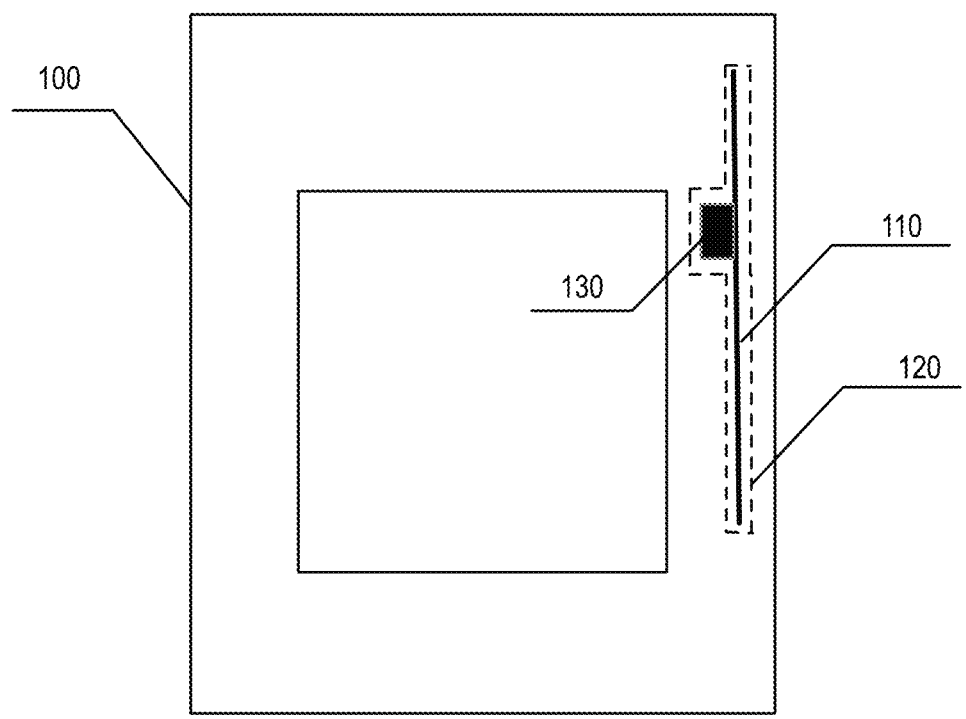
FIG. 12B is a schematic representation of a system variation with a defined PCB cavity having a varied profile.

In a basic defined cavity variation, as shown in FIGS. 12A and 12B, the defined cavity may have a uniform profile or a varied profile. In a uniform profile, the width and shape of the defined cavity along the defined path is of uniform dimensions. The uniform dimensions may function to simplify manufacturing and may additionally more generally accommodate a wider variety of circuitry surfaces 110. As shown in the two exemplary defined cavities of FIG. 12A, a uniform can be used in straight paths and more complex paths. A varied profile preferably has a width and shape of the defined profile that varies along the path. This may be used to accommodate size considerations of specific components of the PCB. As shown in FIG. 12B, a varied profile may include a protruding portion of the defined cavity to accommodate an electronic component 130 that protrudes further from the surface of the PCB. Uniform PCB cavities and varied defined PCB cavities may be utilized as desired with any implementation of this invention.

In general, the defined PCB cavity variations are described as they may be formed where the defined PCB cavity extends from one face of the body into the structure. As such, one preferred manufacturing process to form a defined cavity is subtractive machining, where the defined cavity extends downward into the implant body 100 to form a "slit". Although other techniques (e.g., such as molding around a removable material in a form of investment casting or other techniques) may make other geometry features achievable. This structure of the defined cavity may additionally make the insertion of the PCB a simpler process in that it can be slid into the defined PCB cavity. In some variations the PCB may be folded prior to or as the PCB is inserted. The system preferably includes a sheathing 120, which may additionally function as a cavity seal such as an epoxy, silicone, an attached cap, or other structure to close the exposed portion of the defined PCB cavity.

In some alternate variations, the PCB may be molded within the implant body 100 or enclosed within a multi-part implant body design, wherein the PCB may be partially or completely embedded in the implant body after manufacturing and assembly. In this variation, the defined PCB cavity may be wholly embedded within the implant body such that there are no externally exposed portions of the defined PCB cavity. The defined PCB cavity may still have an internal defined cavity/cavities functioning to house the PCB.

Figure 13A:
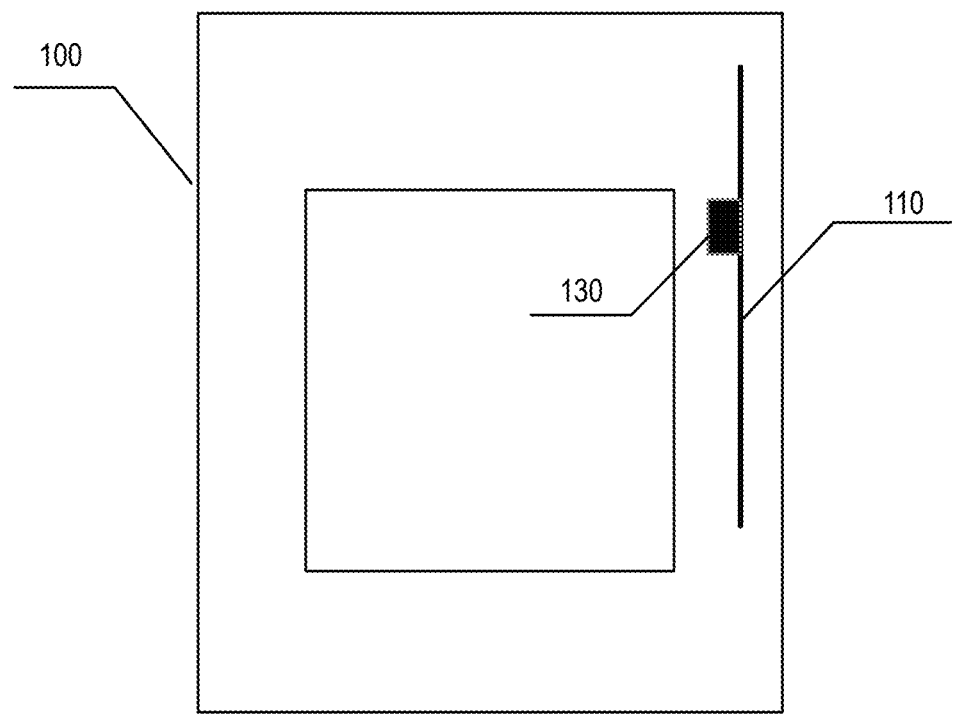
FIGS. 13A and 13B are schematic representations of exemplary systems of preferred embodiments with the PCB embedded along a single path.
Figure 13B:
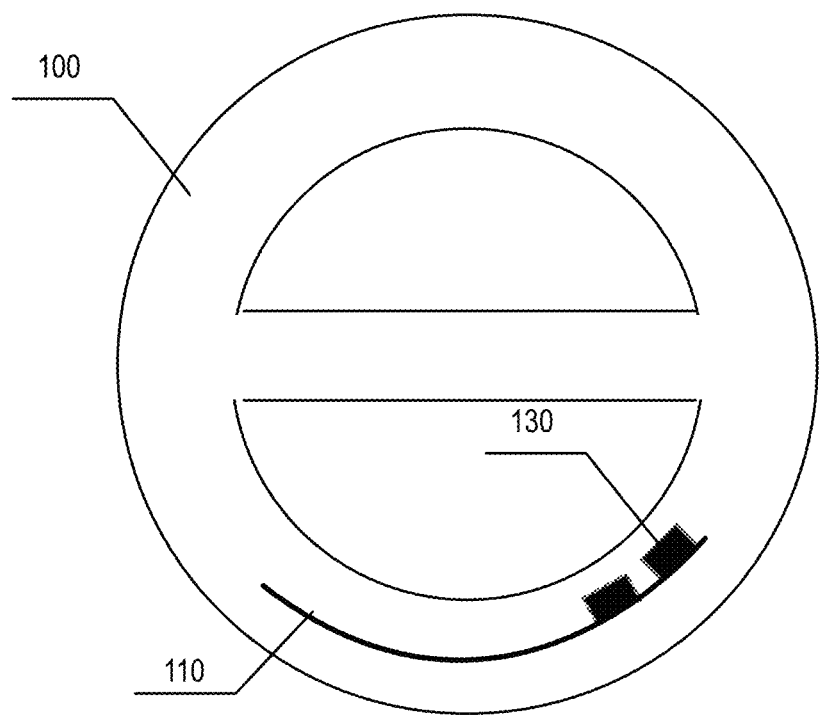

In preferred variations, the PCB is embedded in the implant body 10o along a path. A path may be a straight path as shown in FIG. 13A or a curved path as shown in FIG. 13B. As desired, the PCB may be wholly or partially embedded in the body, wherein each segment of the PCB embedded within the body is embedded along one path (straight or curved). In some preferred examples, multiple straight and/or curved paths may be implemented. The curved path may utilize the bendable nature of the PCB, and therefore places some constraint on the system. For any curved path implementation, the curved path preferably does not have a curvature beyond how far the PCB can bend. Alternatively, the PCB may be printed with a curvature, making a curved path form-fitting.

Figure 14A:
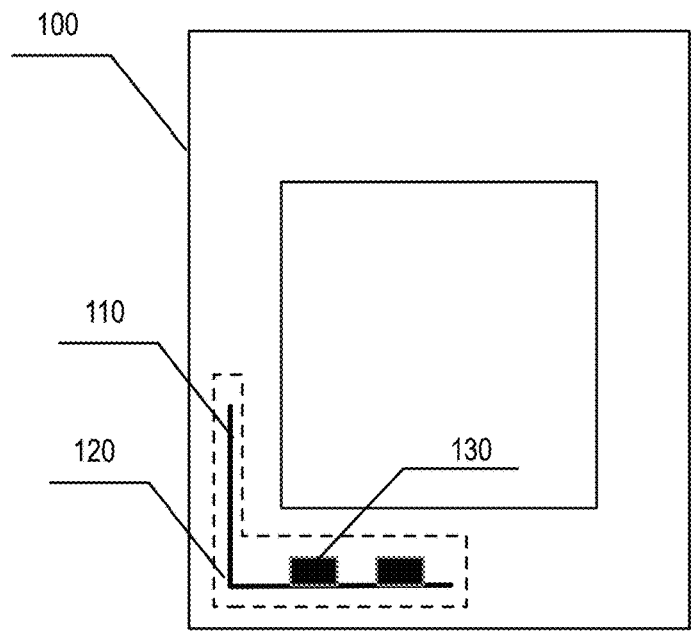
FIGS. 14A and 14B are schematic representations of exemplary systems with a folded PCB.
Figure 14B:
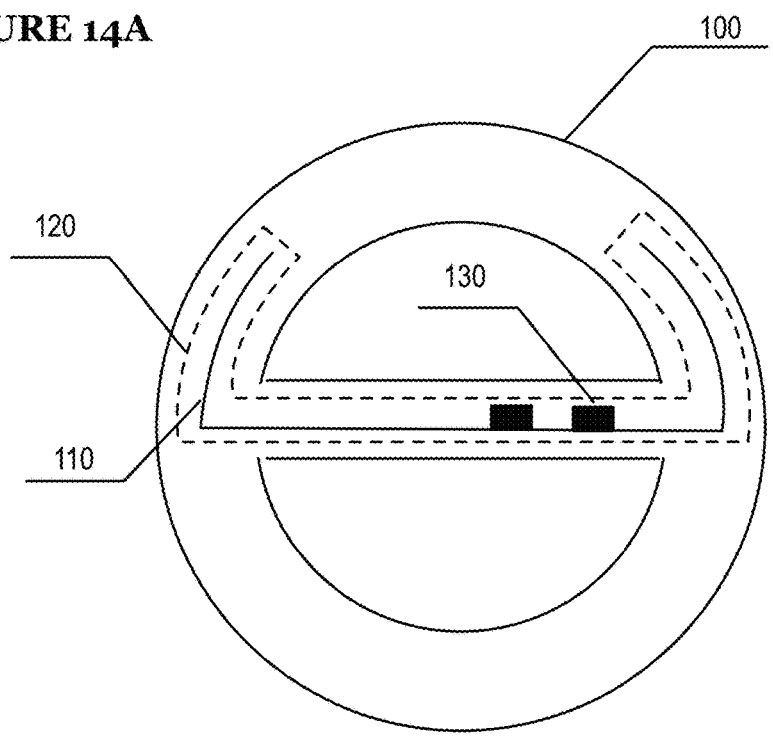

As another variation that further extends the notion of a bending path, the defined cavity may include at least two segments connected along a discrete corner. In such an angled path variation, the PCB is at least partially folded at one or more locations and embedded wholly or partially in a path. That is, the PCB and PCB folded region are embedded within the same defined cavity of the implant body 100. Each segment may be straight or curved. Given a decreased ability to bend for a folded segment of the PCB, the curved path curvature may be further limited for a folded segment of the PCB. An angled path variation may implement the angle to bend around the structure of the implant body 100 as shown in FIGS. 14A and 14B. As shown in FIG. 14A, the defined PCB cavity may have one or more angles and one or more PCB bends establishing two or more path segments and PCB segments. Each segment may be straight or curved; uniform or varied in profile; and/or have any suitable feature. As shown in FIG. 14A, both segments of the PCB can be substantially straight. As shown in FIG. 14B, one segment of the PCB can be straight, and another segment curved.

Figure 15A:
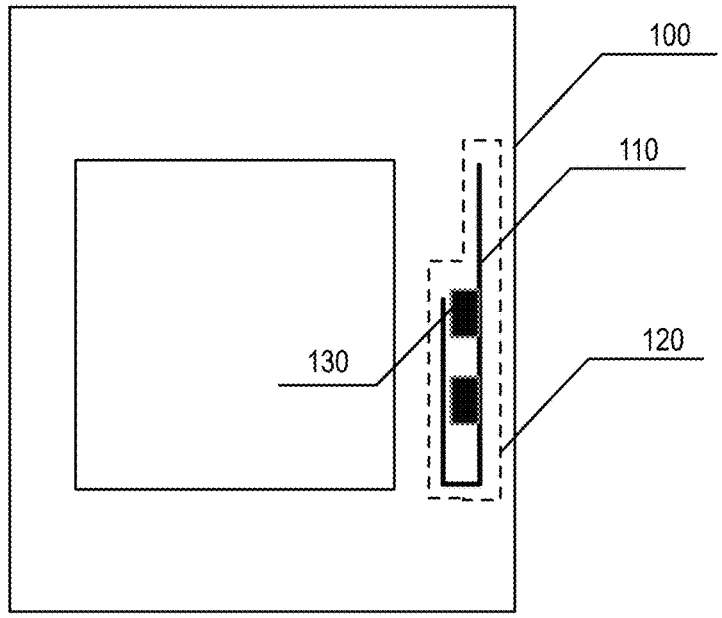
FIGS. 15A and 15B are a schematic representation of exemplary systems PCBs configured with reverse folds.
Figure 15B:
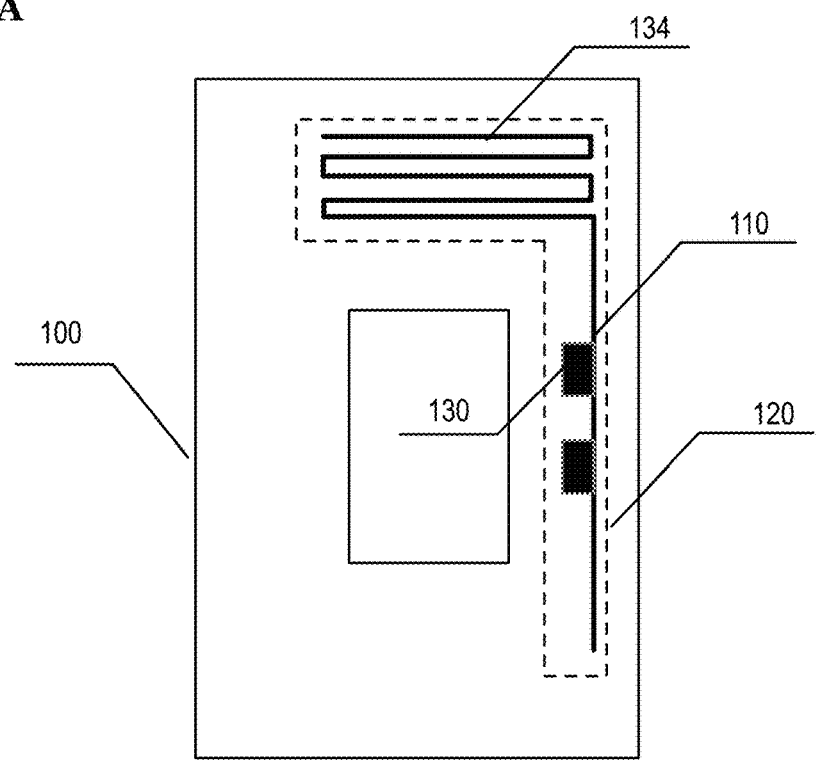

As an additional or alternative variation, the PCB maybe reverse folded (i.e., folded at least once back on itself in an accordion manner) and the defined PCB cavity can accommodate a reverse folded region of the PCB as shown in FIG. 15A. The PCB may be reverse folded any suitable number of times as shown in FIG. 15B. In some variations, the reverse folds may be coordinated with the PCB layout of an antenna component such that the reverse folds create two or more layers of antenna 134 coils. Thus, multi-layer folded PCBs may be implemented to accommodate electronic components 130 that can utilize them (e.g. amplify signal of a multi-layer antenna). Additionally, the multi-layer folded PCB may enable the PCB to fit in geometrically limited spaces (e.g. a rectangular cavity). For example, the PCB may be folded in a configuration so that multiple layers of a circuitry subsystem can be compactly housed within a defined cavity in the form rectangular prism.

Figure 16:
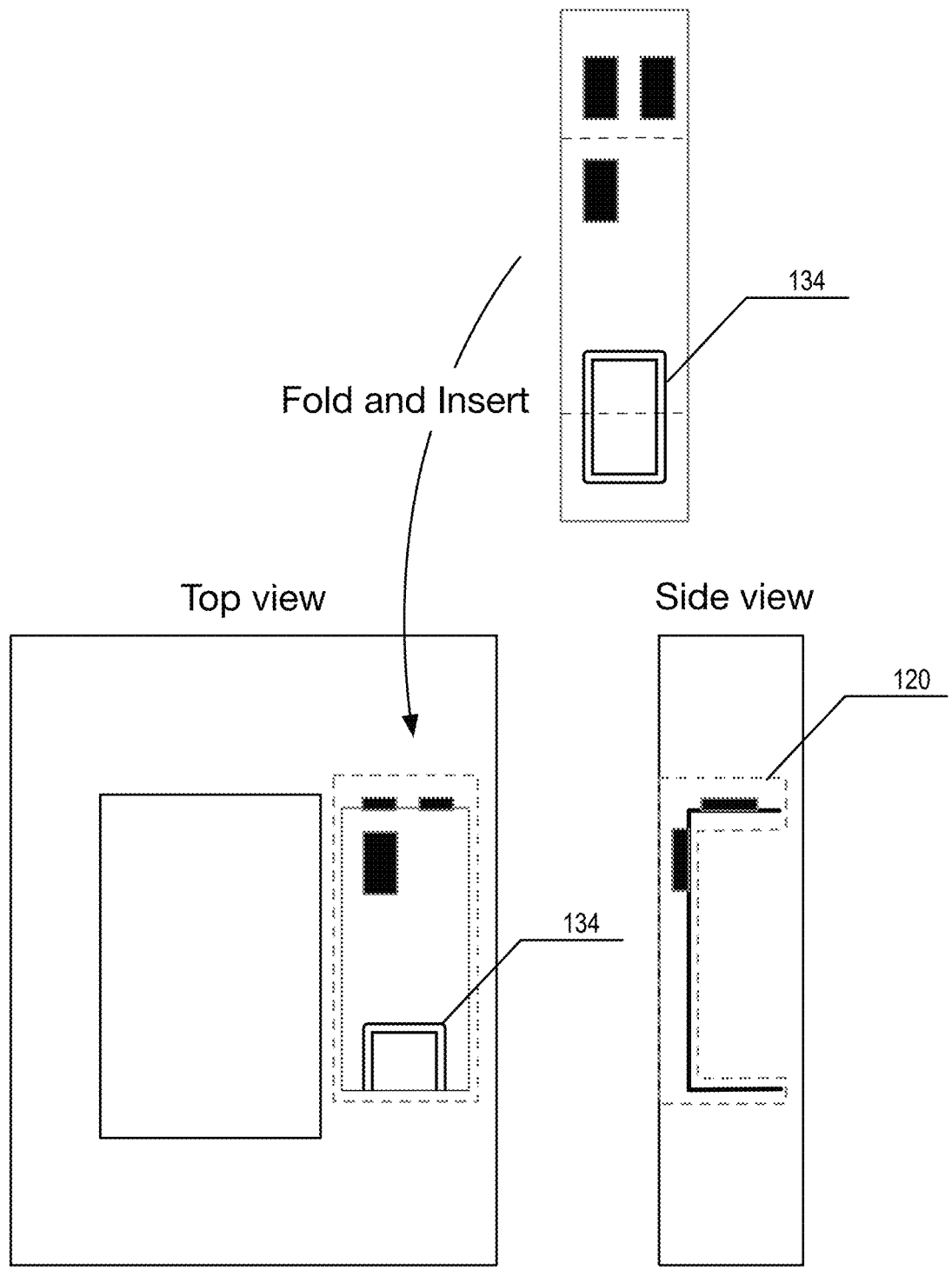
FIG. 16 is a schematic representation of an exemplary system with a PCB in a table geometry of a preferred embodiment.
Figure 17:
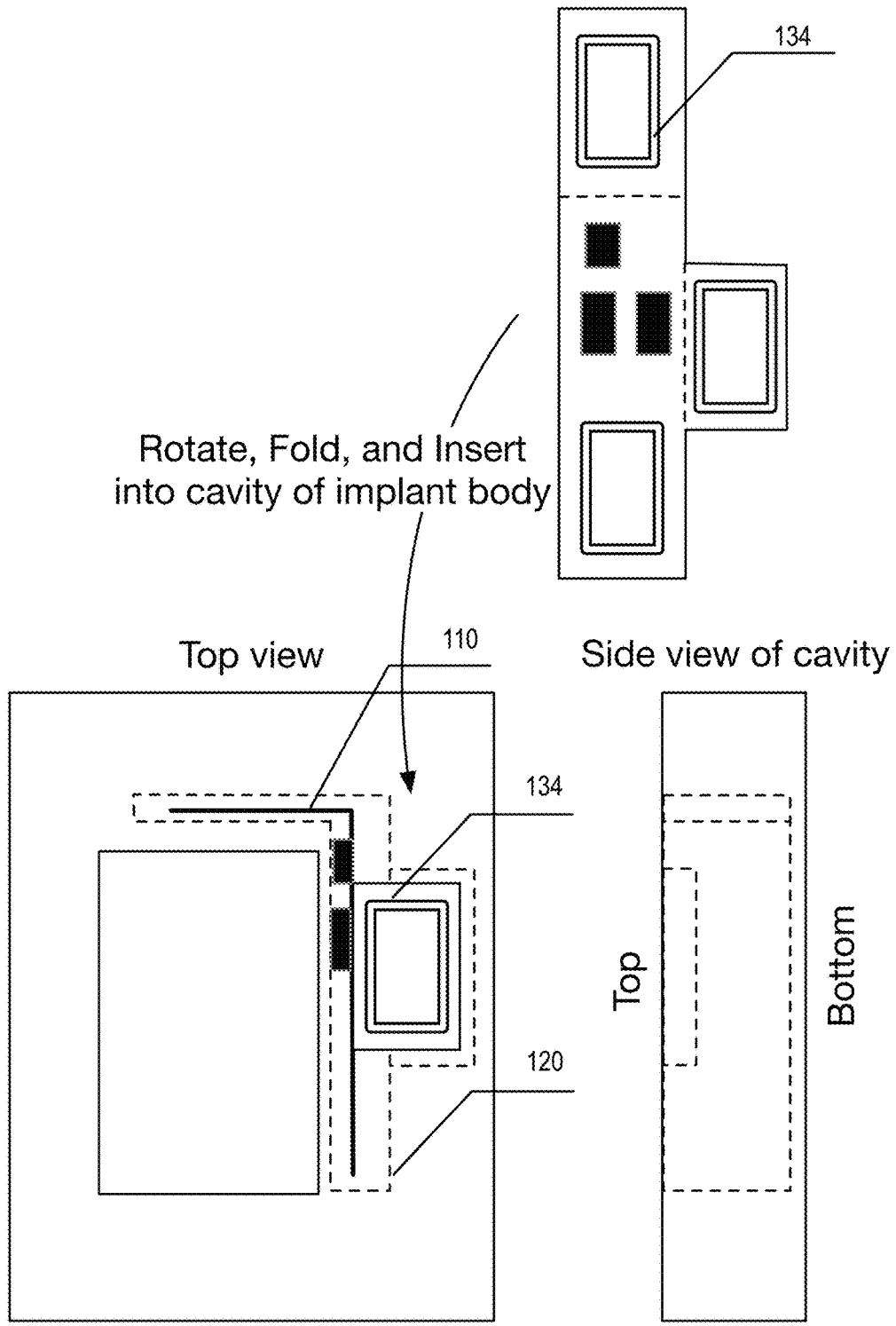
FIG. 17 is a schematic representation of an exemplary system applying multiple PCB cavity and PCB configurations to achieve antennas in three orthogonal planes within an implant body.

In another variation, the defined cavity may make use of different cavity depths. This may function to enable a fold axis along the surface face of the PCB. With a defined cavity with different depths, the PCB may be folded or bent along a fold axis so that at least one face is oriented such that the normal to the face is in the direction of a defined axis of insertion. As shown in FIG. 16, a defined cavity may have "table-shaped" geometry and the PCB can be bent on either end so that the middle portion has a face normal to the direction of insertion and that both ends are bent and inserted into a deeper portion of the defined PCB cavity. In the table geometry, at least part of the PCB is lying flat along the top, bottom, or side of the implant body 100. Either one or both regions adjacent to the lying flat segment may then be bent into the implant body 100. One or both sides may be alternatively embedded along curved paths. In some variations, the PCB may include multiple adjacent table folds wherein the PCB is bent over the edge of the implant body 100, thereby covering multiple sides of the body. As shown in FIG. 17, a custom PCB surface shape can be used to enable multiple folding strategies. In this exemplary variation, three antenna 134 structures may be oriented to be mutually orthogonal.

To summarize PCB placement and folding, in preferred implementations of the system, any combination of bends, folds, reverse folds, and table folds, along straight and/or curved paths may be utilized; taking into consideration the position of the electronic components 130 on the PCB. In other variations, the implant body 100 may be formed as a multi-part design that is adhered, sonically welded, attached, or otherwise connected together. An internal cavity may be defined within one or more of the body parts such that in enclosing the body parts, a PCB can be internally encased. In another variation, the implant body 100 may be overmolded onto or around the PCB. In one implementation, a molding frame (i.e. sheathing 120) may be connected around the PCB. The molding frame functions to structurally support the PCB and optionally shield the PCB during the overmolding process. The PCB placement geometries described herein may be used in both variations.

In some variations, the system of can include sheathing 120. Sheathing 120 functions as a physical support and/or enclosure for system subcomponents that provides protection and/or support to the medical implant and/or system subcomponents. The sheathing 120 may be incorporated for any circuitry system 105 component. The sheathing may be particularly useful for implementation with the circuitry surface 110, wherein the sheathing may provide a protective enclosure (e.g. a heat resistant silicone sheath/enclosure) and/or increased tensile strength (e.g. a strong titanium support) for the circuitry surface 110.

Figure 18:
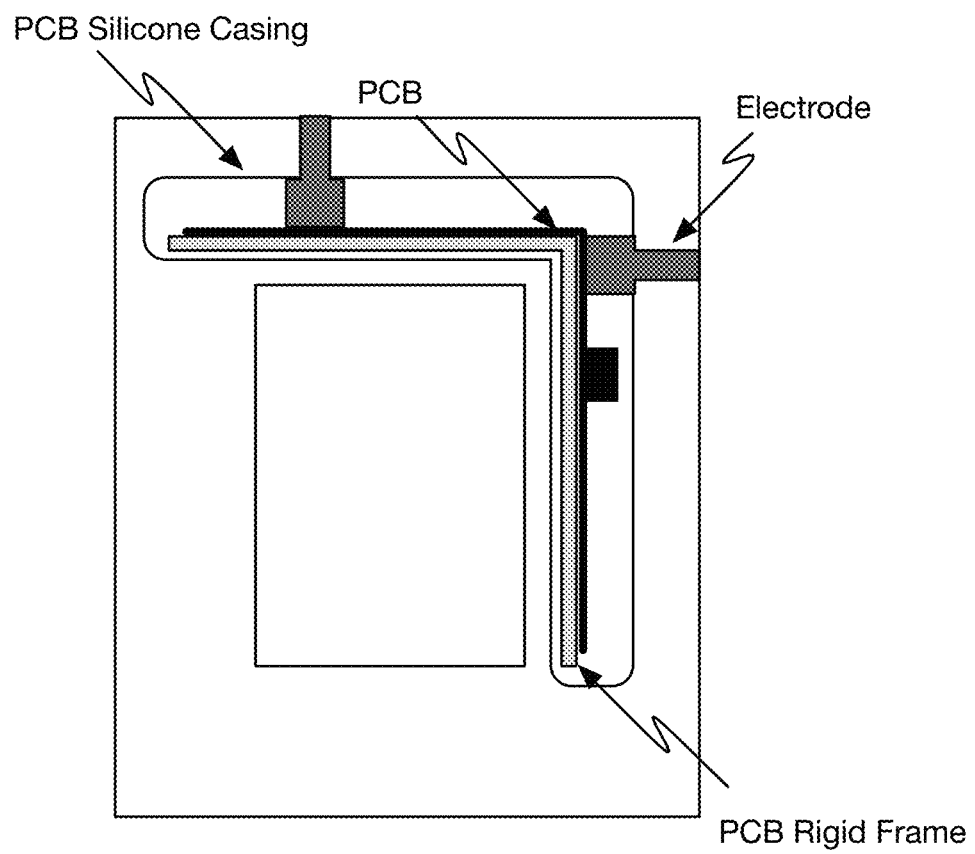
FIG. 18 is a schematic representation of an exemplary system illustrating integration of two electrodes into the implant body.

In variations where the sheathing 120 provides a protective enclosure, the portion of the circuitry surface 110 at least partially embedded within the implant body 100, may be "sheathed" such that the circuitry surface 110, and attached electronic components 130, are enclosed within the sheathing 120, thereby potentially protecting the components from implantation conditions, and/or protecting the components during building/molding of the medical implant. In variations, where the sheathing 120 provides tensile strength to the circuitry surface 110, the sheathing 120 may comprise a rigid structure along the circuitry surface 110, as shown in FIG. 18. In preferred variations, the protective enclosure sheathing 120 may additionally aid in completely filling the defined cavity that the circuitry surface 110 is embedded in (e.g. through a molding process).

In variations where the sheathing 120 provides tensile strength, the sheathing may comprise a support structure. This may be particularly the case for variations that include a PCB with many folds or bends. Support structures function to assist maintain the load and shape of the circuitry surface 110 and ease manufacturing. Support structures are preferably localized in regions of the circuitry surface 110 which are populated with components but may be located in any other desired region (e.g. PCB components in the casing 140 of the medical implant). The sheathing 120 may additionally function to decrease the likelihood of mechanical failure for electronic components 130 in, or along, the circuitry surface 110.

The sheathing support structure may be implemented to provide support for other circuitry system 105 components, electronic components 130, and for other general medical implant components. As part of a sheathing support structure, materials may be combined to enhance the mechanical properties of the implant body 100 and/or subsections thereof. In some variations, the circuitry surface 110 may include one or more sheathing 120 layers composed of a material with higher (or lower) mechanical strength/stiffness etc. than the material making up of the remainder of the implant body 100. In this manner, the sheathing support structure may increase the tensile strength of both the circuitry surface 110 and implant body 100. The support sheathing 120 may be an external sheathing, on the surface of the implant body 100; an internal sheath, within the implant body; or both interior and exterior sheaths. The support sheathing 120 may additionally be a full or a partial sheathing of the circuitry surface 110, thereby fully or partially encasing the circuitry surface 110 while providing additional support to the implant body 100. For example, if the volume of the implant body 100 is primarily made using PEEK the sheathing 120 may be made using titanium or carbon fiber reinforced PEEK. In some variations, wherein the implant body 100 is partially hollowed out to incorporate the circuitry surface 110 (i.e. creating the defined cavity), using a material that is mechanically stronger than the implant body 100 composition, may ensure that the hollowed-out section is less mechanically compromised or even mechanically stronger relative as compared to the rest of the implant body 100. A sheathing 120 made of a mechanically stronger material may ensure the mechanical integrity of the implant body 100 manufactured with an appropriate form factor featuring dimensions appropriate for human implantation (for example ensuring that thicknesses, such as those marked by 3-4, 3-5, 3-6, 3,7 in FIG. 6, are not greatly expanded to compensate for weaker mechanical properties caused by hollowed out sections).

The sheathing 120 may additionally or alternatively comprise a protective structure. The protective structure may function to protect the circuitry surface 110 and electrotonic components 130 on the circuitry surface, both during normal implementation, and during construction of the medical implant (e.g. the protective sheathing 120 may protect electronic components 130 from breaking down due to high temperature molding processes. The system may include a sheathing 120, which can protect the circuitry surface 110 embedded within the implant body 100. Additionally, the sheathing 120 may electronically insulate components, thereby protecting circuitry (e.g. circuit system and electronic components) from conductive components. The system may include a circuitry surface 110 that is either partially or fully embedded within the implant body 100. The sheathing 120 may provide a complete enclosure of the region of the circuitry surface 110 that is embedded within the implant body 100. Alternatively, the sheathing 120 may entirely enclose the circuitry surface 110, including regions not embedded within the implant body 100. Alternatively, the sheathing 120 may only partially enclose regions of the circuitry surface 110 embedded within the implant body 100 (e.g. protect only antenna components on a PCB). The implant body 100 may have a groove or slit as a defined circuitry surface 110 cavity within its structure. The circuitry surface 110 may be housed within the defined cavity. The defined cavity may be formed as part of the mold of the implant body 100. Alternatively, a secondary manufacturing process may cut or remove material to form the defined cavity in the implant body 100. As part of embedding the circuitry surface 110 within the defined cavity, the embedded regions of the circuitry surface may be enclosed in a protective structure sheathing 120. The sheathing 120 preferably comprises a non-reactive, non-toxic material. In some variations, the sheathing 120 protective structure is composed of silicone, wherein the circuitry surface 110 is fixed within the defined cavity of the implant body 100 by overmolding the circuitry surface into the defined cavity using silicone. Alternatively, the sheathing protective structure may be composed of: epoxy, resin, or other applicable material.

In variations where the circuitry system 105 comprises a PCB, the sheathing 120 may include a PCB envelope, which functions to entirely or at least partially envelope the PCB as a sheathing protective structure. The PCB envelope preferably functions as an inner cover and at least a second external facing implant body 100 encases the PCB envelope. The PCB envelope is preferably a silicone material that is molded or formed around the PCB. The PCB envelope with the enclosed PCB can be inserted into the defined cavity. The silicone mold may serve to insulate the electronic components 130 during manufacturing processes and to electrically insulate the electronic components from other conductive components. The silicone mold may additionally or alternatively function to contain the elements of the PCB in the event of failure or during extraction of the implant by a doctor. A rigid backing or frame may additionally be included or connected to the PCB. The rigid frame can function to enhance the structural integrity of the PCB and possibly the resulting implant. As shown in the example of FIG. 18, the sheathing 120 may comprise both a support structure (i.e. the PCB rigid frame long pieces placed along the PCB, and a protective structure (i.e. the PCB silicone cover). In this example, the support structure may be constructed using polyimide or other appropriate material.

Figure 19:
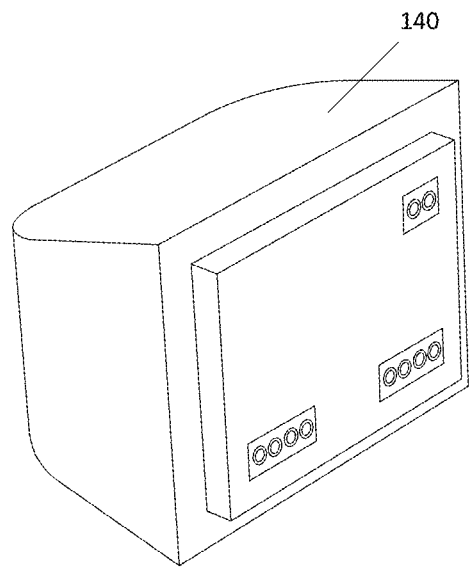
FIG. 19 is an illustration of a casing of one variation of a system, first showing the external view of the casing, and then showing the internal components within the casing.
Figure 19:
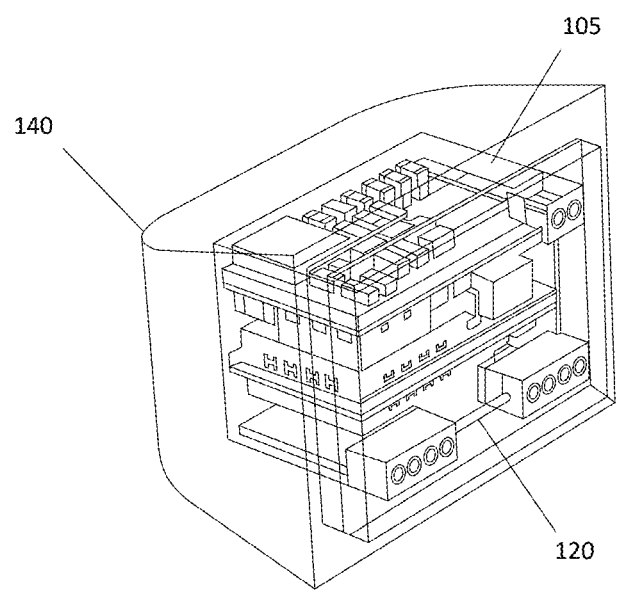

One variation of support structures may be observed in the bottom image of FIG. 19, wherein support structure sheathing is implemented to support a PCB in a casing 140 that is external to the implant body 100. In a variation comprising a multiple layered PCB embedded in an external casing 140, the sheathing 120 may comprise rectangular support structures between the top, middle, and bottom layer of the PCB. The PCB shown may be produced by populating only one side of the PCB with components. Alternatively, both sides of the PCB may still have electronic components 130, wherein the sheathing 120 is placed in between the components to protect and support the multiple layers of electronic components.

Additionally, sheathing 120 for the PCB in the casing 140 may include a protective sheathing. In one variation, the PCB within the casing is overmolded with silicone, or silicone is cast around the PCB prior to insertion into the casing 140. This may provide an additional layer of protection for the PCB. Additionally, the protective sheathing 120 may isolate and insulate the PCB from the casing 140. This may be of particular importance when the casing is also utilized as an electrode.

The system of a preferred embodiment includes at least one electronic component 130. In preferred variations, electronic components 130 include: a set of electrodes 132, and an antenna 134. Additional electronic components 130 may be added to the system as desired and dependent on implementation. Dependent on implementation and the type of electronic component 130, electronic components may be directly connected to the circuitry system 105, or may be connected to the circuitry system 105 through wiring 150.

For spinal cage variations of the system, electronic components 130 may include any desired electronic components. For the spinal cage preferred variation, the electronic components 130 may include: electrodes 132 (transmit electricity into tissue, sinking or sourcing current from and to the tissue), grounding electrodes (establish ground voltage), capacitors (store external energy), implant transmitters/receivers, rectifier circuit, control circuitry (manages control of components), monitoring circuitry (sensor components), impedance measuring circuitry, antennas 134 (transfer power and/or information to and from the medical implant), battery (long term power source), capacitors (short term chargeable power source), and/or other suitable electronic components 130. Electronic components 130 may be arranged on or around the circuitry system 105 as desired. In variations that include a PCB, electronic components 130 may be less flexible than the PCB itself, thus certain regions of the PCB may be less flexible depending on the housed electronic components.

As part of variations that include a PCB, and similar to PCB placement and geometry, electronic components 130 may be spatially arranged by component heights such that subgroups of components with high effective heights (compared to other components) are grouped in the same subsection of a folding pattern of the PCB. For example, taller components may be positioned next to each other so that only one subsection of the PCB may have to accommodate the taller height when folded. In some examples (e.g. where parts of the board contain only routing leads), the PCB may have a particularly thin profile, enabling the PCB to be folded multiple times without significantly effecting the PCB thickness.

Figure 20:
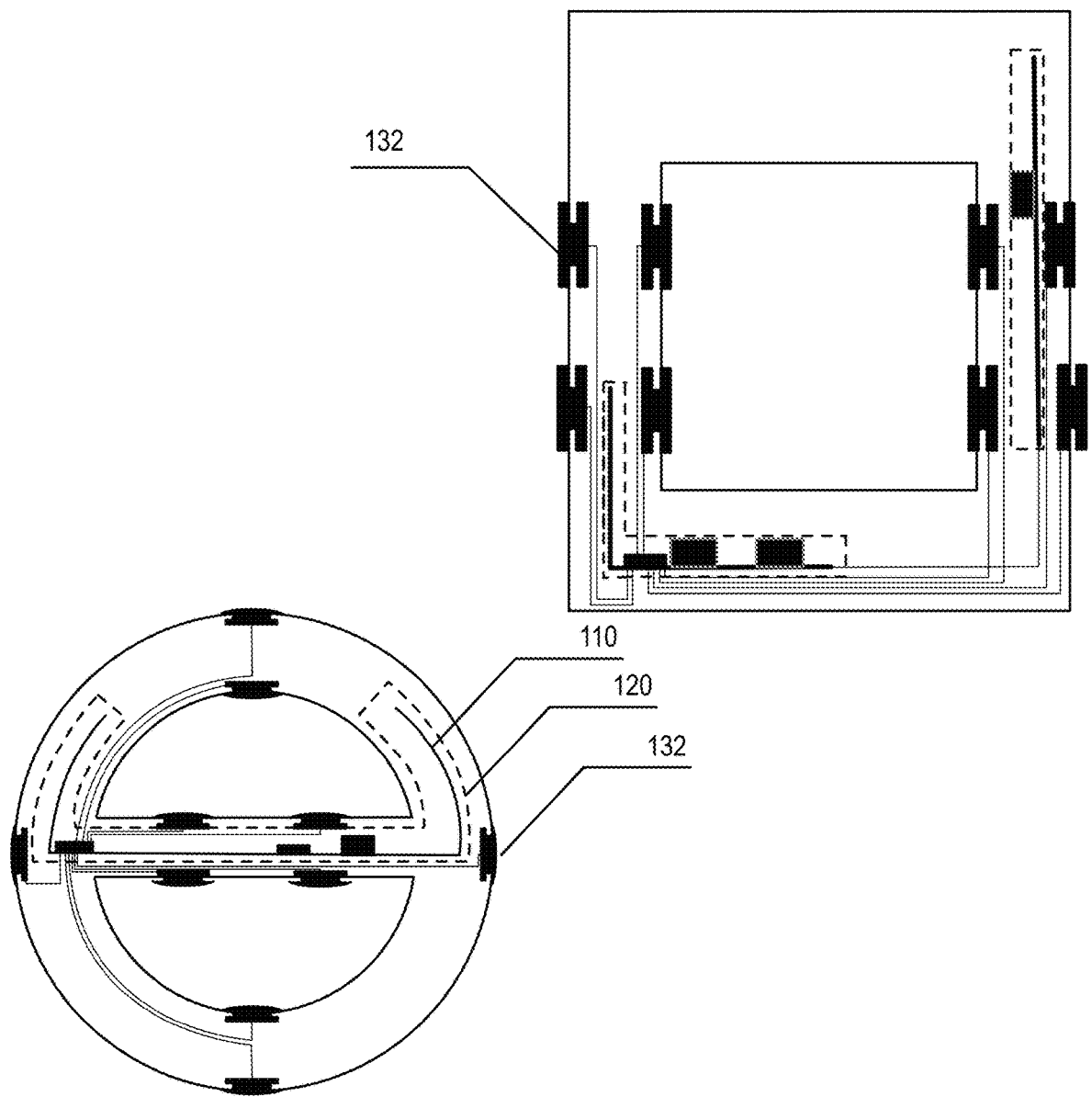
FIG. 20 includes schematic representation of systems with integrated electrodes.

Electronic components 130 preferably include a set of electrodes 132. As shown in FIG. 20, preferably, a set of distinct electrodes 132 is exposed at one or more sites along the surface of the implant body 100. In variations that include a PCB, the electrodes 132 are preferably conductively coupled to the PCB and configured to be controlled by the PCB (and/or electronic components 130 on the PCB). The PCB can preferably provide the power and signal to establish an electrical potential at one or more sites and/or to make an electrical measurement (e.g., voltage or current). An electrode 132 is preferably made of a conductive material. Electrodes 132 are preferably composed of electrically conducting elements (e.g. titanium or platinum).

Figure 28:
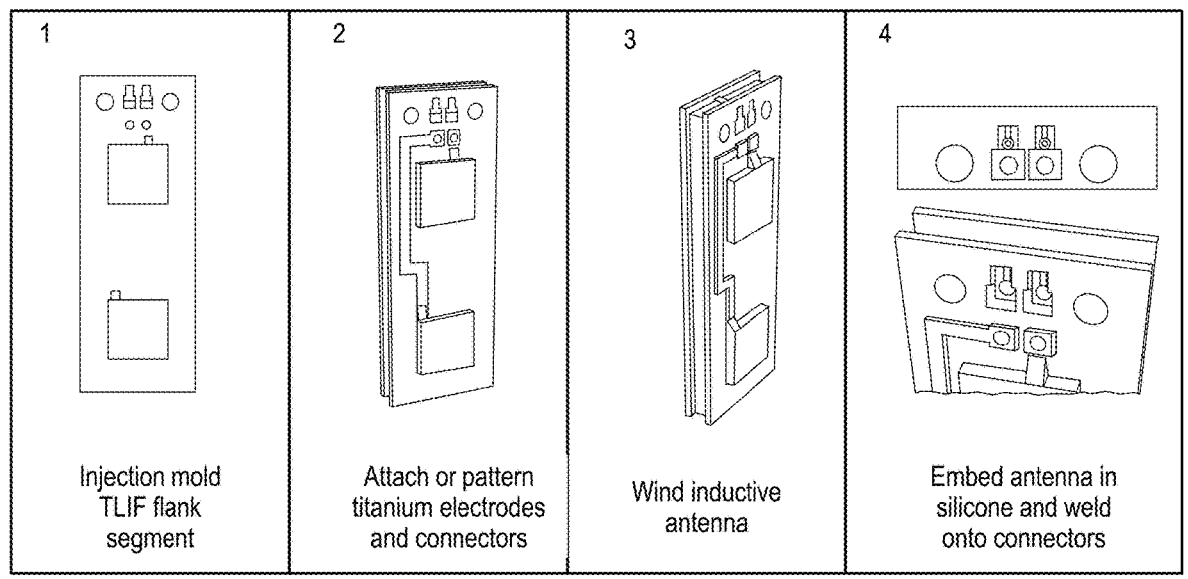
FIGS. 28 and 29 are a stepwise example illustration of a method implementation.

In one variation, at least one surface of the electrode 132 is exposed externally at the surface of the implant body 100. As shown in FIG. 18, an electrode 132 may include an internal shoulder structure connected to an exposed electrode structure. The internal shoulder structure is preferably internally oriented in the implant body 100 and functions to prevent removal of the electrode 132. In one implementation, the electrode 132 is initially connected to an internal structure and an external body is over molded around the electrode. Electrodes may constitute volumes separate from the PCB that are attached following PCB manufacturing. Electrode 132 may also be directly printed onto the PCB substrate preferably as part of manufacturing the PCB, or alternatively as a separate step to metalize the appropriate regions of the PCB using a metal suitable for forming an electrode site (e.g. titanium and/or platinum). The electrode 132 and/or it's connections may additionally be printed directly onto the implant body 100, for example titanium and/or platinum may be deposited onto a PEEK implant body 100 and/or casing to form electrodes 132 and/or leads/connectors (FIG. 28). Printing of conductive components on or within an implant body are preferably conductively coupled to wiring or other conductive elements that connect the printed conductive element to the circuitry system 105. If printed onto a flexible or semiflexible substrate, these electrodes 132 may also bend/fold across non-normal surfaces of PCB casings and/or implant bodies.

As shown in FIG. 20, in a second variation, electrodes 132 may be exposed external of the implant body 100, while a part of the electrode is embedded within the implant body itself. This may aid in holding the electrode 132 in place to prevent movement of the electrode. Each electrode 132 may then be electrically connected to a circuitry surface 110 (e.g. through wiring 150) that contains electrical generating components. Electrodes 132 and their connections may additionally be printed directly onto the implant body 100, for example titanium may be deposited onto a PEEK implant body and/or casing to form electrodes and/or leads/connectors. If printed onto a flexible or semiflexible substrate these electrodes 132 may also bend/fold across non-normal surfaces of PCB casings and/or implant bodies.

Electronic components 130 preferably include an antenna 134. As shown in FIGS. 2, 7, and 16, antennas 134 may be positioned and oriented in many different ways dependent on implementation. Antennas 134 function to send and receive external communication (e.g. to control electrode 132 function) and/or to receive external power (e.g. to inductively charge capacitors, power the system, etc.). An antenna 134 may comprise a single body antenna, as shown in FIG. 16, or the antenna may comprise multiple bodies, as shown in FIG. 17, wherein the antenna comprises three orthogonal antennas on a PCB. The antenna 134 may be built on the circuitry surface no (e.g. an antenna that is printed onto a PCB), or independently positioned on the implant body 100 (e.g. embedded within an implant body cavity).

The antenna 134 may be implemented in any desired configuration. An antenna 135 can be implemented as a conductive path which will generally be tuned to a resonant frequency. The antenna could be a coiled loop, a meandering line conductive path, and/or any suitable type of antenna. In one variation, as shown in FIGS. 7 and 8, the antenna comprises wired loops around the circuitry surface 110 embedded along two lateral walls of the implant body 100. The antenna 134 may then be electrically connected to other electronic components 130 (e.g. embedded in a connected casing 140) by wiring 150. In a second variation, the antenna 134 may be printed, or attached, onto a circuitry surface 110 (e.g. IC or a PCB). As an antenna 134 is more flexible, the antenna may, or may not, be positioned on a bent part of the circuitry surface 110. In one example of the second variation, the antenna 134 may comprise multiple antennas that span three-dimensional space. In this example, the PCB may be folded such that the PCB has at least one normal surface to all three space dimensions, as shown in FIG. 17. An antenna 134 may then be printed on each normal surface of the PCB such that the antenna spans all space dimensions. Generally, the PCB may have any number of folds, wherein all folds combined, at least, span all space dimensions. Antennas 134 may then be mounted on sufficient PCB surfaces such that the antenna spans all space dimensions. In a third variation, the antenna 134 may comprise connected, or disjoint, structures along folds of a PCB folded in an accordion manner, as shown in FIG. 15B. That is, the antenna 134 may leverage the PCB reverse folding to create an extended antenna, wherein loops (or other another geometric structure) of the antenna are linearly positioned along each segment of the reverse fold. In one example of the third variation, the antenna 134 may comprise a multi-layered geometry wherein adjacent layers of the PCB contains a part of the antenna, thus forming a relatively three-dimensional antenna comprising stacked planar folds. This type of antenna 134 may function to improve signal transfer as compared to relatively planar antennas.

Figure 21:
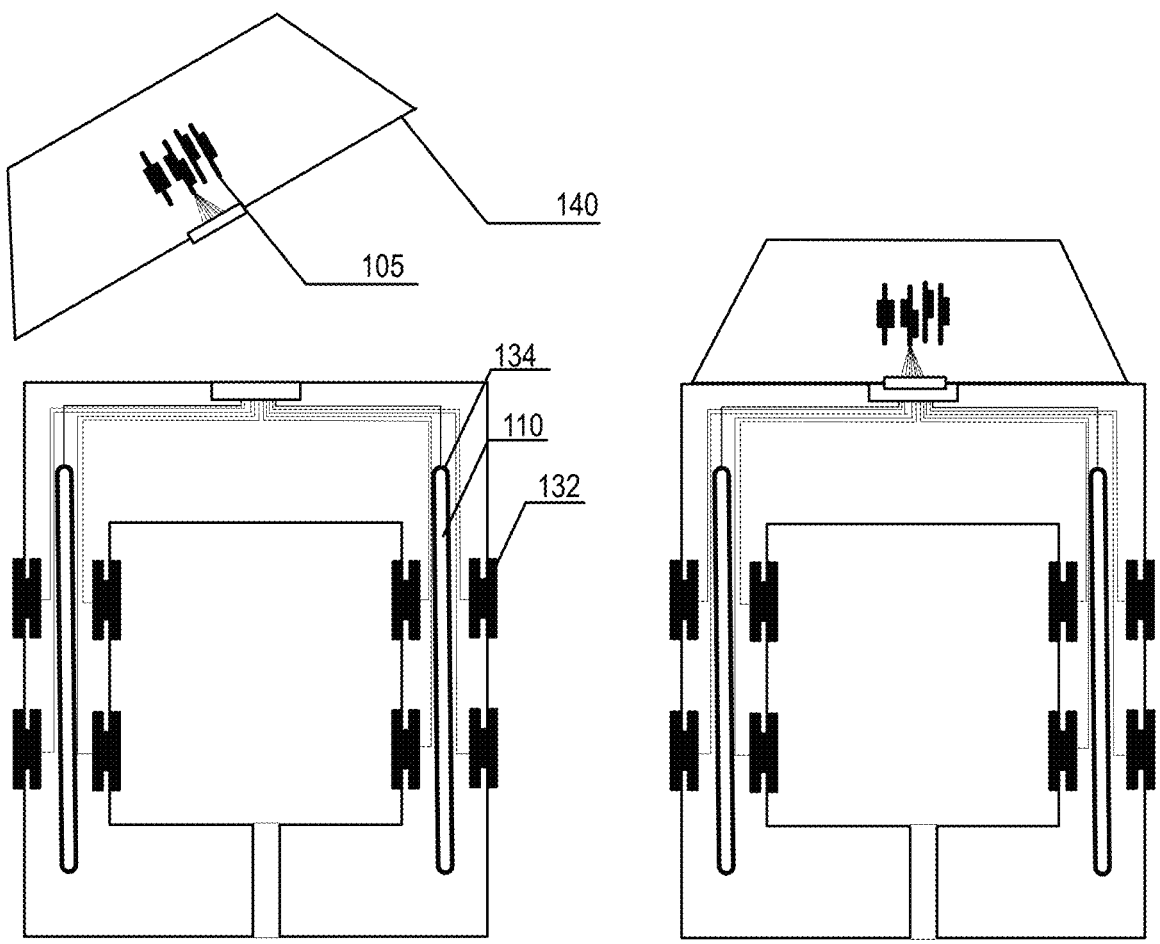
FIG. 21 is a schematic representation of one variation of a system with a circuit system within a casing that connects to circuitry surface components within an implant body.
Figure 22:
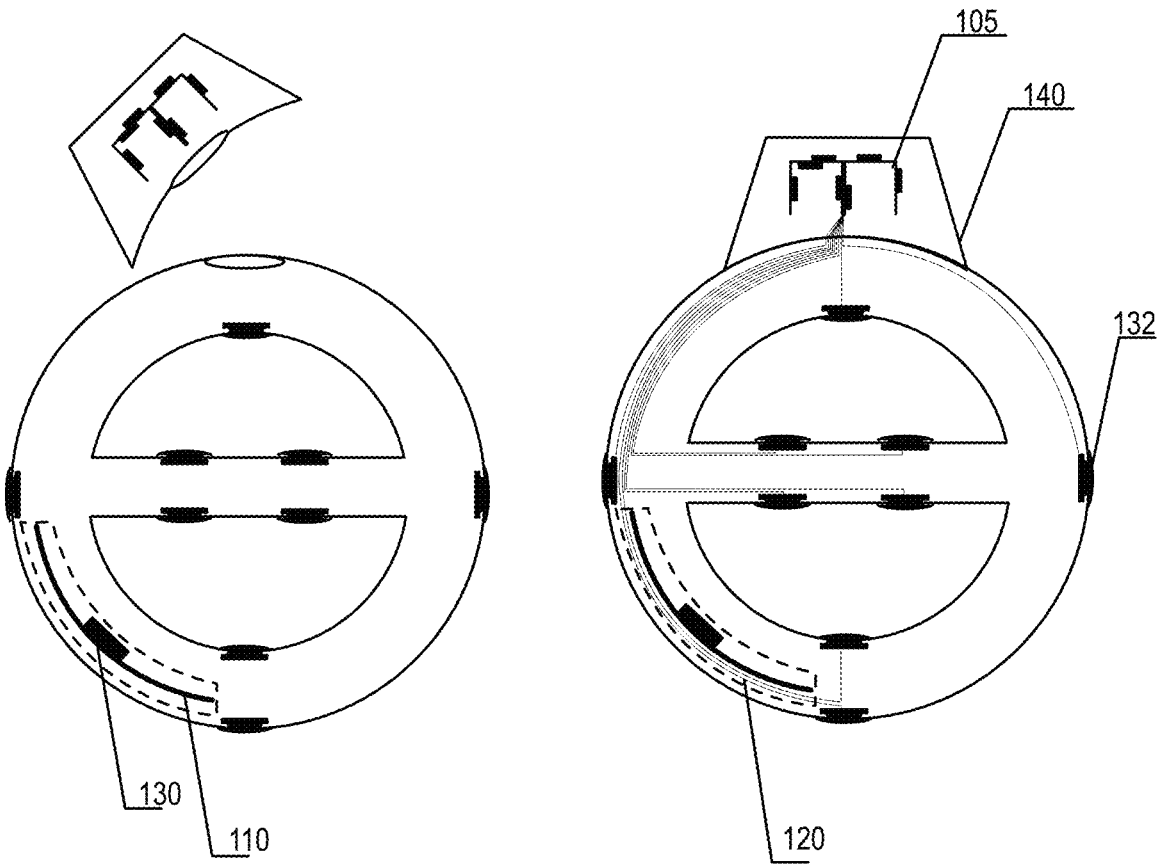
FIG. 22 is a schematic representation of another variation of the system.

In some variations of the system, the system includes a casing 140. As shown in the illustrations of FIGS. 8, 9, and 19, the casing 140 functions as a distinct body structure that can house electronic, or other components, outside and adjacent to the rest of the implant body 100. The casing 140 may be integrated with rest of the implant body 10o during the manufacturing process. FIG. 21 and FIG. 22 show example schematics of different implant bodies 100 with casings 140. These schematics show the casings 140 prior to, and after they are integrated with the implant bodies 100. In preferred variations, the casing 140 is integrated with the implant body 100 irreversibly, such that they form a single structure. Alternatively, the casing 140 may be incorporated as a distinct body structure that can be connected, or disconnected from the implant body 100. The casing 140 may be constructed of PEEK but may alternatively be constructed of alternative materials such as titanium that may or may not be platinized.

In some variations, the casing 140 may not add substantially to the size and/or shape of the implant body 100. That is, the casing 140 preferably adds no limitations to the desired volume and/or desired shape of the implant. The casing 140 is physically adjacent and connected to the implant body 100. The casing 140, in some variations, may constitute some of the outermost surfaces of the medical implant. Alternatively, the casing 140 may be adjoined to the implant body 100 from an interior cavity (e.g. the casing 140 may be positioned within the spinal cage of a medical implant) The casing 140 may be positioned anywhere along the implant body 100 as desired, limited by functionality and size limitation. As shown in FIG. 21, the casing 140 may be positioned on the lateral exterior of the implant body 100; along a shorter side of the implant body 100. Alternatively, the casing 140 may be positioned along the longer side of the implant body 100. Alternatively, the casing 140 may be positioned in the interior of the implant body 100, along a flat or curved surface of the interior cavity.

In some implementations, the casing 140 may constitute one or both thicker short ends (e.g. 3-4, 3-5 in FIG. 6) of the implant body 100 (representing the nose/front and the tail/back section in the case of a lateral, PLIF, OLIF or TLIF cage, as shown in FIG. 9. The nose and tail may have increased dimensions and made hollow to house the PCB (possibly folded). Furthermore, if the medical implant needs to be removed or drilled out, a mechanically strong casing 140 may increase the probability of the casing remaining intact during the procedure which may reduce the likelihood of elements of the PCB becoming exposed during or following the removal procedure. In this manner, the casing 140 may assist in protecting a patient from potentially toxic PCB components both during regular operation, and during implantation or removal of the implant.

In some variations that include a casing 140, the circuit system 105 may further comprise casing circuitry subsystem. In one implementation, the casing circuitry subsystem includes a PCB component, wherein the PCB is enclosed within the casing 140 and electronically connected to one or more circuitry surface 110 in the implant body 100. That is, the casing 140 may include an enclosure that can hold casing circuitry subsystem (e.g. IC, PCB, ASIC, etc.), and/or other electronic components 130, wherein the electronic components may be on or separated from the casing circuitry subsystem. In variations that include a casing 140 with one or more PCB components, the PCB(s) may have any of the properties as described above. That is, the PCB may be rigid, flexible, or semi-flexible (e.g. have foldable regions and rigid regions). The PCB may additionally be folded and/or shaped in any desired to geometry or configuration, as described previously. In one example, as shown in FIG. 21, the casing PCB comprises a semi-flexible PCB that is folded in an accordion type configuration. In another example, as shown in FIG. 22, the casing PCB comprises a semi-flexible PCB that is folded in a table type configuration.

The enclosure may include a latch opening, that can be opened or closed. Preferably, the enclosure is hermetically sealed using for example a laser welder. Alternatively, the casing 140 comprises two or more parts that combine to form the external housing. Electronic components 130 may be placed within the enclosure prior to combining the parts together. Preferably the two or more parts are then sealed together, hermetically sealing electronic components within the enclosure.

In some other preferred variations, the casing 140 does not include an enclosure for adding or removing components. In these variations, the casing circuitry subsystem (e.g. PCBs) and/or electronic components 130 may be embedded within the casing(s) 140 during construction of the casing(s) 140 (e.g. through an overmolding process).

Figure 23:
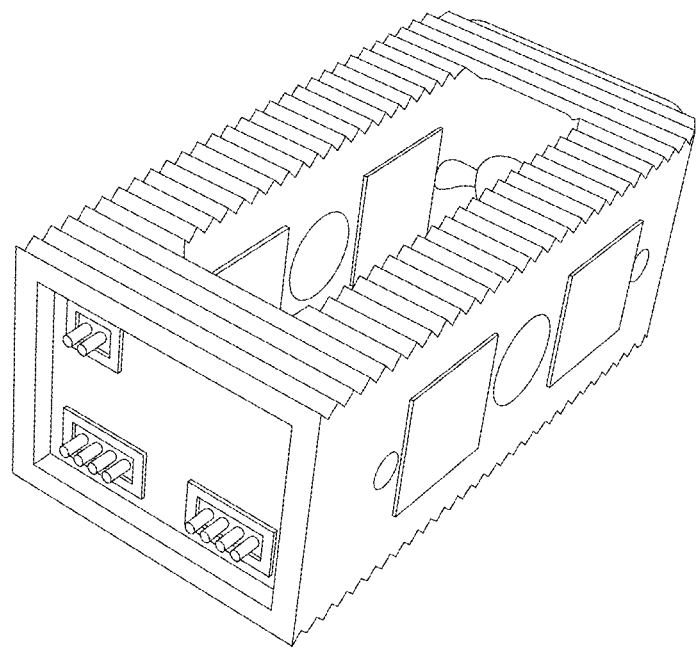
FIG. 23 is an illustration of an implant body with exposed connectors to connect to a circuit system within a casing.
Figure 25:
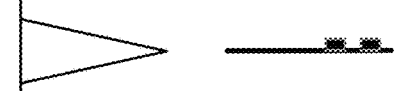
FIG. 25 is a flowchart of one variation of the method applied to embedding a circuitry surface in an implant body.
Figure 25:
Figure 25:
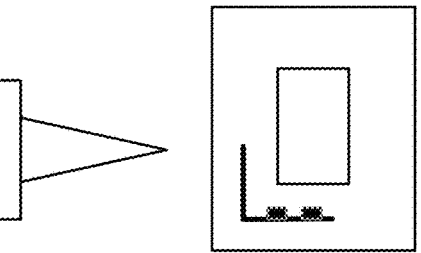

In conjunction with embedded electronic components 130, the casing(s) 140 preferably includes at least one connector that enables electronic connection with the implant body 100. The connector functions to connect the PCB and electronic components 130 in the casing 140 to electronic components on or within the implant body 100 (e.g. electrodes 132 and antenna 134). FIG. 19 shows an image of a casing 140 with connectors that would connect to the rest of the implant body 100 through a set of complementary connectors, as shown in FIG. 23. In preferred variations, once the casing 140 is integrated with the implant body 100, the connectors and complementary connectors are sealed and form a single structure. For some variations, wherein all circuitry system 105 components are embedded within the casing 140, the casing has a sufficient number of connectors to connect to all electronic components 130 of the system (e.g. all electrodes 132, antennas 134).

The casing 140 may be produced in a separate process than the rest of the implant body 100, wherein the two parts may then be joined/attached/adhered after each have been produced in separate processes. The casing 140 and the rest of the implant body 100 may alternatively be produced in inseparable steps such as overmolding the implant body 100 onto the casing 140 or 3D printing the casing onto the rest of the implant body. The casing 140 may also include anchors to help attach to the rest of the implant body 100. Anchors may directly attach to a body produced in a separate step. They may also help anchor the casing 140 to the rest of the implant body 100 after the rest of the implant body has been overmolded or otherwise joined onto the casing 140.

Figure 31:
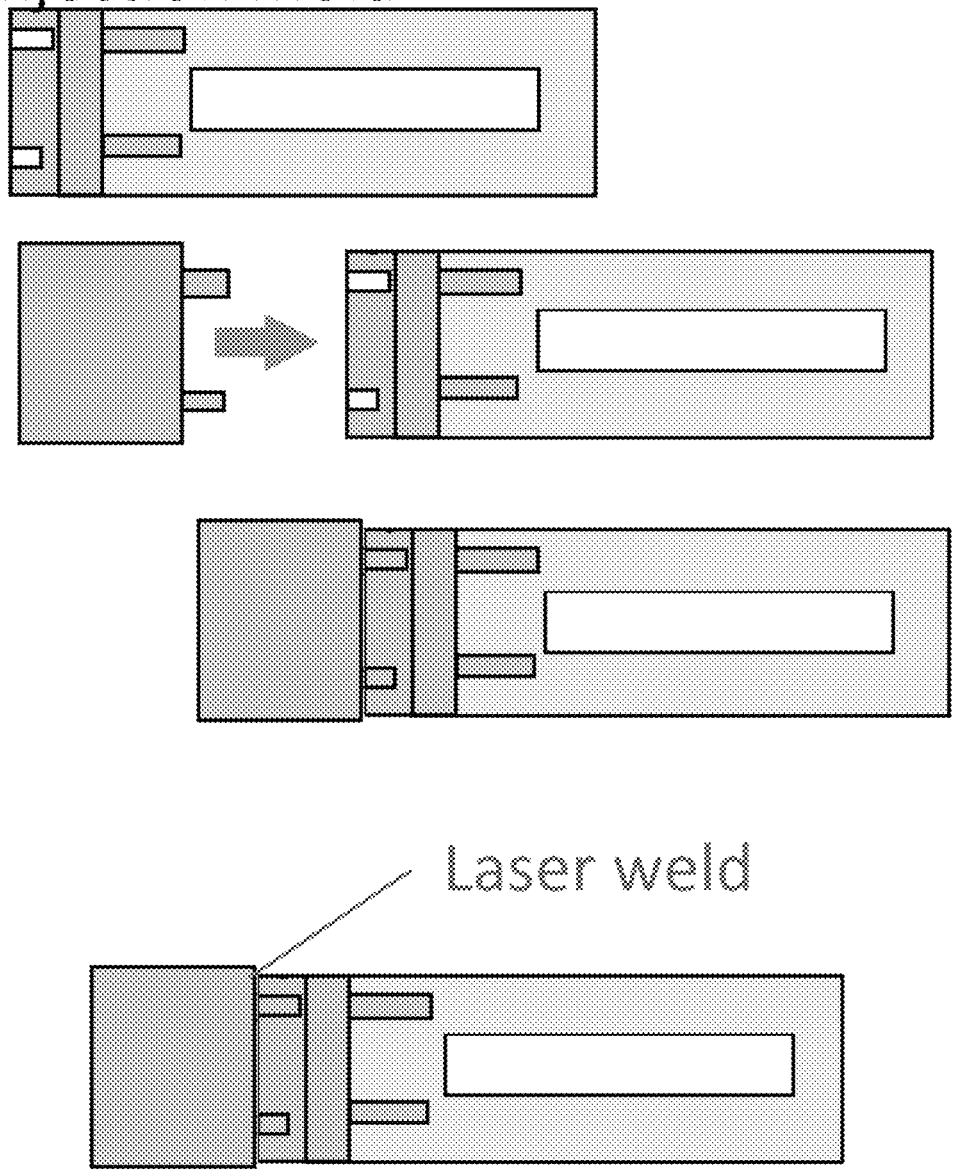
FIG. 31 is a schematic description of combining the implant body and the casing.

The casing 140 is preferably permanently integrated or fixed, in place, to the implant body 100. The casing 140 may be sealed, locked, or connected using some any desired mechanism, such as first welding the casing to the implant body 100, and then overmolding both structures together. Dependent on the implementation, the casing 140 may be a temporary, or permanent fixture to the implant body 100. In one example, the casing 140 is a permanent fixture and is sealed, by welding the casing to the implant body 100. In one example, as shown in FIG. 8, wherein the casing is welded to the nose of the implant body 100, the casing 140 may be welded or otherwise connected to the implant body with an offset from faces of the implant body 100 on which sources of force or stress will primarily be directed when implanted in the body. For example, the casing 140 can be welded with an inset offset away from the top and bottom faces of a spinal cage implant body 100 where forces from adjacent vertebrae will be exerted (FIG. 31). In this way, this may reduce forces that may weaken the connection of the casing 140 and the implant body 100.

In one variation, the casing may not be permanently attached. For example, in a spinal cage implementation, the casing 140 may be utilized during spinal growth treatment. Once treatment is complete and the spinal cage is sufficiently connected to the patient vertebrae, the casing 140 may be separated and removed from the patient without disturbing the rest of the implant body 100. The potential temporary nature of the casing 140 may thus be leveraged to utilize helpful, but potentially toxic, electronic components 130 for medical treatment (e.g. batteries). In an alternative preferred implementation, the potential temporary nature of the casing may be leveraged to use components with limited lifespans (e.g. sensors). By exchanging the casing 140, non-functioning components may be periodically replaced, and/or upgraded during treatment.

In variations where the casing 140 is temporary, the casing may additionally be detachable from the implant body 100. Detachable casings 140 may enable the addition or removal of individual casing components. In such a variation, the PCB or other electronic portions of the system may be included, embedded, enveloped or otherwise contained within a modular subsection of a casing 140. If any part of the medical implant needs to be removed and/or drilled out following implantation, the casing 140, or even multiple casings, may be removed separately. to decrease the likelihood of elements of the circuitry system (e.g. PCB) being exposed during or following the removal procedure. Additionally, or alternatively, new casing 140 components may be added to the implant to add or replace functionality to the implant.

The casing 140 may provide additional functionalities to the implant. In some variations, the casing 140 may include additional features. For example, in the case of a mechanically stronger casing 140 that is made out of a metal, such as titanium and/or platinum and has a surface that is at least partially exposed to the body following implantation, the casing 140, or subsections of the casing, may additionally be used as electrode(s) 132 to source and/or sink current. For example, in some variations, the casing 140 or one or more subsection(s) of the casing 140 can be used as an electrode 132 wherein the electrode portion of the casing is made of a conductive material and conductively coupled to a control system. The electrode 132 may be configured as an anode or a cathode or as a switchable electrode wherein a digital or analog switching system can be used to alter the polarity of the electrode (e.g., changing state between a source and sink).

As a distinct body or implant subcomponent, the casing 140 may provide positional utilization as an electrode 132. For the spinal cage implementation, the casing 140 may provide a region distal to regions of desired bone growth. One or more electrodes 132 may be positioned on, or in, the casing 140. This electrode function may be complementary functionality to electrodes 132 in bone growth regions. For example, electrodes 132 within the spinal cage implant body 100 may function as an electric source, wherein the casing 140 electrode 132 would be activated to function as an electric sink. In some implementations where the casing 140 is produced using titanium (which may be platinized), part of, or the entirety of the metal casing may function as an electrode 132.

In variations wherein the casing functions as an electrode source/sink, and/or the casing includes other electrodes, the casing circuitry subsystem may include a protective sheathing. In one example, the PCB within the casing 140 may include protective sheathing (e.g. overmolded with silicone), thereby insulating the PCB from any unwanted current. Additionally, sheathing 120 may provide an additional barrier in circumstances where the casing 140 may break. The casing circuitry subsystem may otherwise be conductively isolated from a conductive casing element 140. In some variations, the casing 140 may be conductively connected as an electronic component 130 (e.g., an electrode) of the circuitry system 105.

The system of a preferred embodiment includes wiring 150. Wiring 150 functions to connect circuits and electronic components 130 that are not physically connected. In some variations, the implant body 100 may include pathways, wherein wiring 150 may be drawn through to connect components, as shown in FIG. 7. Alternatively, wiring 150 may be held in place as the implant body 100 is built around the wiring.

The system may be implemented for a broad range of electrically embedded medical implants. Herein, one spinal cage example, as shown in FIG. 9, is presented. In this implementation, the system comprises a relatively rectangular spinal cage implant body 100; a circuitry surface 110 comprising two planar surfaces embedded in the two longer lateral sides of the rectangular spinal cage, and wherein each planar surface contains four electrodes 132 and an antenna 134; a casing 140 physically connected to a shorter lateral side of the rectangular spinal cage, wherein the casing encloses a multi-layered PCB; and wiring 150, connecting the multi-layered PCB to the antenna and electrode components. In this example, each circuitry planar surface contains four electrodes 132 and an antenna 134, such that from each planar surface two electrodes 132 are exposed on the exterior lateral surface of the implant body 100, extending normal and outward from the planar surface; and each planar surface contains two electrodes 132 exposed on the interior lateral surface of the implant body 100, extending normal and inward from the planar surface. Additionally, each planar surface has an antenna 134 wrapped around and along the circumference of the circuitry planar surface along the same dimension of the planar surface. Each antenna 134 is wrapped around the circuitry lateral surface in the same plane as the lateral surface, such that the antenna spans the majority length of the implant body 100. As the electrode 132 and antenna 134 are the only electronic components 130 embedded within the implant body 100, this example has no requirement for protective sheathing 120. Dependent on the specific implementation, this example may still comprise support sheathing 120 to provide the implant with greater tensile strength, and/or include protective sheathing to better assist in fixing the circuitry surface 110 in place. Additionally, the PCB within the casing 140 may have sheathing 120 (e.g. silicone) to better protect and/or insulate the PCB. This sheathing 120 for the casing 140 components may help protect, or provide additional protections, for components that may be harmful to a patient. In some implementations, the antenna 134 may be embedded in silicone sheathing 120 to fix it in place. The silicone sheathing may enable use of antenna materials that may be potentially harmful to a patient. Additionally or alternatively, the antenna 134 may be composed of bio-friendly material, such as gold or platinum iridium. As the electrodes 132 are directly exposed to human tissue, they will preferably be composed of non-harmful materials (e.g. titanium, gold, platinum iridium).

In variations that include a casing 140 element, the system can preferably include a circuitry system 105 that partitions the electronic components 130 between casing circuitry subsystem that is contained and housed in a structurally strong and sealed casing 140 and a bio-compatible electronic components 130 that are integrated with one or more circuitry surfaces 110. Electronic components 130 that include non-biocompatible materials or properties (e.g., would be toxic if exposed or leaked into the body) can be securely housed in the casing 140. The electronic components 130 of electrodes 132 and/or an antenna 134 can be made of biocompatible conductive materials and without the use of materials that would be toxic.

3. Method

A method for manufacturing a medical implant device with embedded electronic components functions to incorporate at least one circuit component into the body of an implant that protects the electronics during manufacturing and operation. In particular, the method for manufacturing the medical implant device enables a process for embedding at least one circuitry surface along a path of an implant body that is built around the circuitry surface. The method may also involve a multi-stage process wherein circuitry subsystems are embedded into different implant body components of a medical implant device and then integrated together.

The method may be used in the production of a medical implant device with cohesive integration of electronic components, such as electrodes and/or antennas, and the structural body component(s). In particular, the method can be used in the manufacturing of a load-bearing medical implant device (e.g., a device with at least one load-bearing implant body) with integrated electronics. The method is preferably implemented in the manufacturing, assembly, and/or other form of production of a medical implant device such as the system described above. However, the method may be used in the production of any suitable type of medical device. In particular, the method may be used in the production of load bearing medical devices, where the purpose of a load bearing device may not only be to house electronics, but also serve as a scaffold for tissue growth and/or mechanical stabilizer and/or serve as a vessel for graft material. In addition to the method process variations outline herein, the method can additionally include the forming and/or implementing of any of the system configurations and variations described herein.

In a first method, the method details manufacturing a medical implant device with an embedded circuit involving fabrication of an implant body. In a second method, the method details manufacturing a medical implant device with an embedded circuit post-fabrication of an implant body. Either method or a combination of the methods may be used to manufacture a system of preferred embodiment as described above.

The term "implant body" as used in the method will be used to generically refer to the entire implant body as described in the system, the casing as described in the system, and/or a subsection of either component. For example, implant body may refer to the entire implant body, but may equally refer to one flank segment of the implant body, as shown in step 1 of FIG. 28. An explicit distinction is made between the two implant body components only for the integration of the components together, or to specify specific build requirements of implant body subcomponent. For example, for the manufacture of a medical implant device that has a casing, a distinction is made for integrating the casing with the implant body as described in the system.

The term "circuit", as used in the method, will be generically used to refer to any circuit (e.g. integrated circuit), circuit board (e.g. printed circuit board), and/or portion of a circuitry system or subsystem used in a medical implant device.

The method may be implemented as a single process, wherein the implant body construct components are created simultaneously or a multi-step repetition of the method, wherein the method is implemented for the build of separate implant bodies which are then integrated together and/or implemented for the manufacturing of one implant body with multiple distinct circuit systems or multiple connected circuit subsystems. The method may be implemented with a system wherein the medical implant device comprises an implant body and/or one or multiple casings. As mentioned previously, in implementations wherein the medical implant device includes a casing, and/or in implementations wherein implant body subcomponents are manufactured separately, the method may further include a step to integrate the medical implant device components. For example, for a casing implementation, the method further includes integrating the implant body with a casing.

As shown in FIG. 24, a first method for manufacturing a medical implant device with an at least a partially embedded circuit, includes: constructing a circuit Silo and building an implant body around the circuit S120. The first method functions in creating a medical implant device by fabricating the implant body so as to embed the circuit within the implant body.

Figure 26:
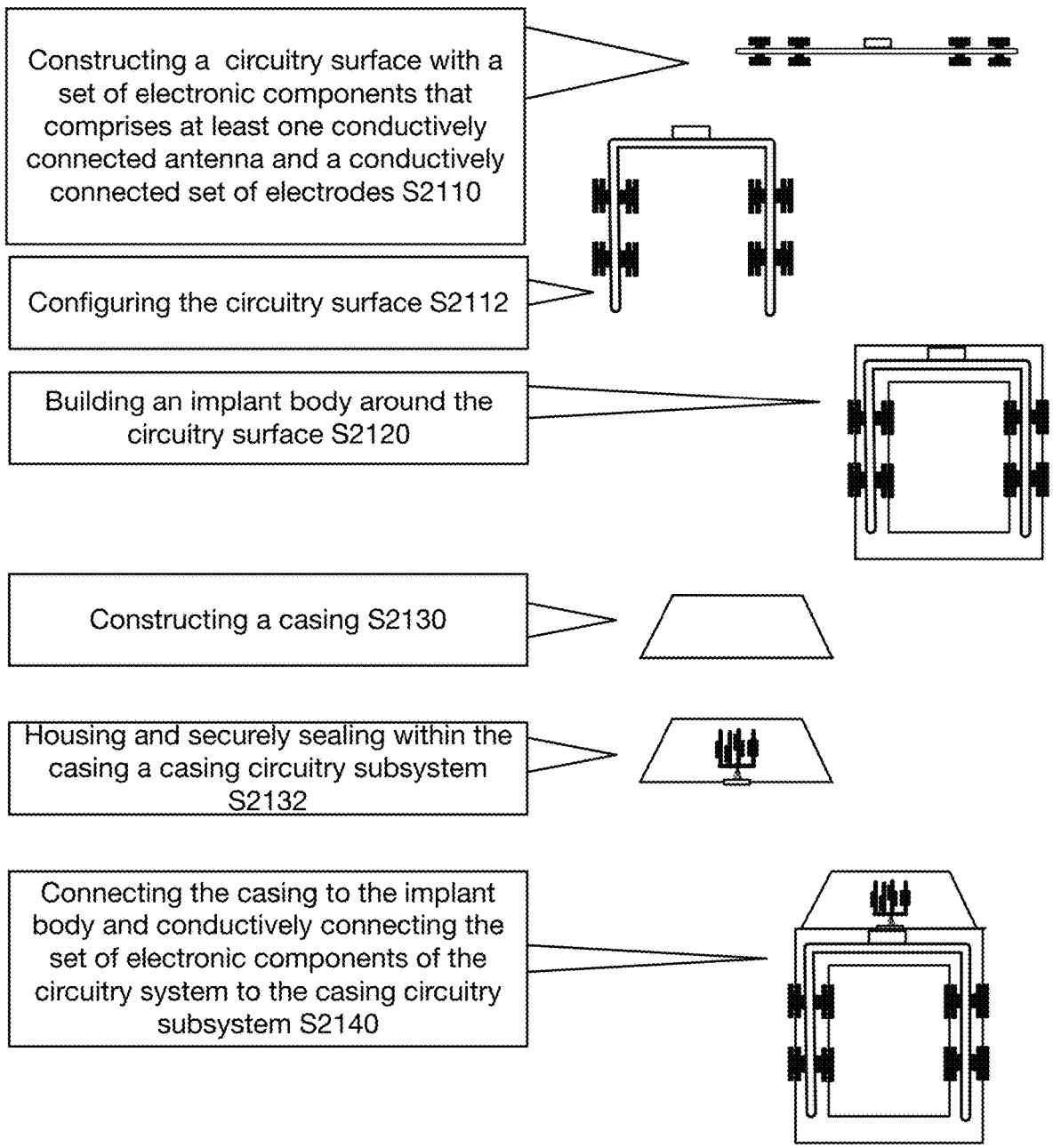
FIG. 26 is a flowchart of one variation of the method applied to a medical implant device with a casing connected to a circuitry surface embedded in an implant body.

In a first variation, the first method may be applied to the embedding a circuitry surface in an implant body. Accordingly, the method can include constructing a circuitry surface and building an implant body around the circuitry surface. As shown in FIG. 26, this may be more specifically applied to the manufacturing of a medical implant device with incorporated electrodes and/or an antenna by: constructing a circuitry surface with a set of electronic components that comprises at least one conductively connected antenna and a conductively connected set of electrodes S1110; configuring the circuitry surface along a path S1112; and molding an implant body around the circuitry surface S1120. This method may be applied to embedding a PCB-enabled circuitry system within a PEEK implant body. In this variation, the method can include assembling a circuitry system on the circuitry surface, which may be used if a PCB element is used as a circuitry surface. This method may also be applied to embedding a circuitry surface with only biocompatible electronic components such as conductive elements forming an antenna and/or electrode components, where that electronic components of the circuitry surface may be conductively connected to some other portion of a circuitry system.

In variations that include a casing, the method further includes integrating the casing with the implant body. As shown in FIG. 26, a method variation may then accordingly include: constructing a circuitry surface with a set of electronic components that comprises at least one conductively connected antenna and a conductively connected set of electrodes S2110; configuring the circuitry surface S2112; building an implant body around the circuitry surface S2120; constructing a casing S2130; housing and securely sealing within the casing a casing circuitry subsystem S2132; connecting the casing to the implant body and conductively connecting the set of electronic components of the circuitry system to the casing circuitry subsystem S2140. In some variations, the casing circuitry subsystem may contain all non-biocompatible electronic components of a circuit system of the medical implant device (or at least a substantial portion such as greater than 95%). Similarly, the electronic components attached to the circuitry surface may be made of biocompatible materials.

In some variations, the method may be implemented for each implant component separately, prior to combining the implant body. In these variations, the method may comprise: for each implant body subcomponent, constructing (or otherwise obtaining) a circuit; for each implant body subcomponent, building an implant body subcomponent around the circuit; and integrating all implant body subcomponents.

Block S110, which includes constructing a circuit functions in obtaining the electronic functional component(s) of the medical implant device. Constructing a circuit S110 preferably includes obtaining and/or assembling a circuit (e.g. a printed circuit board) with all the necessary/required electronic components desired for the implant body construct. Constructing a circuit S110 may include obtaining multiple circuits to be embedded in a single implant body.

Constructing the circuit preferably comprises printing, producing, or acquiring a circuit (e.g. circuit board of desired shape and components). That is, for a PCB variation, beyond a typical sheet-like PCB, printing or purchasing a circuit board of desired shape includes obtaining a PCB with layout and features accommodating bends, folds, and table geometries, as described above.

Constructing the circuit can more specifically include constructing a circuitry surface such as discussed in the system above. The circuitry surface can include a set of electronic components, which preferably includes a set of electrodes and/or one or more antennas. The set of electrodes and/or the antennas can be conductively connected through one or more conductive connections (e.g., wires or conductive bonds). The set of electrodes and optionally the antenna may also be structurally held in position through the circuitry surface or an attachment to the circuitry surface. The electronic components can be conductively connected to a circuitry system that is part of the circuitry surface. For example, the circuitry surface may be implemented as a foldable PCB with conductive connections to an antenna and a set of electrodes. The electronic components may alternatively be connected to an electrical connector, which can be connected to another circuitry subsystem such as a casing circuitry subsystem.

In addition to constructing the circuitry surface, the method may include configuring the circuitry surface along a path, which functions to fold and/or orient the circuitry surface for proper alignment prior to building an implant body around the circuitry surface. Accordingly, the method may additionally include folding and arranging a PCB into an intended formation. Various folding patterns such as discussed in the system above may be used.

Block S120, which includes building an implant body around the circuit, functions to embed the circuit within the implant body. Building the implant body around the circuit can be implemented through a variety of manufacturing techniques.

In one variation, building the implant body around the circuit includes molding the implant body around the circuit. More specifically, this includes overmolding the implant body around a circuitry surface and its electronic components. Overmolding over a circuit functions to form the implant body or a sub-structure with an embedded circuit. Overmolding over a circuit substrate may include 3-D printing, injection molding, casting, or otherwise additively forming the implant body around the circuit. Once completed, overmolding the implant body creates the implant body with an embedded circuit with substantially little impact to the implant body shape. In some implementations, the implant body may be substantially a unibody material structure. In some implementations, this material can be PEEK or other biocompatible polymers.

In some preferred variations involving overmolding around a circuitry surface, the method may include protecting the circuit (e.g., the circuitry surface) with temperature shielding material and then overmolding over a protected circuit substrate. The protected circuit substrate may function to limit temperature exposure of the circuit and its electrical components to mitigate risk of component damage resulting from high temperatures.

In some variations, protecting the circuit includes placing the circuit (e.g., the circuitry surface) in a protective envelope/enclosure. In one variation this includes molding the circuit in a flexible non-toxic, non-reactive material (e.g. silicone or another biocompatible material). The silicone or other biocompatible material would function to protect the circuit during the overmolding process.

In some variations, protecting the circuit includes attaching at least a portion of the circuit (e.g., the circuitry surface) to a circuit rigid frame and overmolding around the circuit connected to the circuit rigid frame. This variation is particularly useful for a circuit comprising a PCB. In one implementation, the circuit rigid frame may be built from PEEK, but any suitable material may be used. Alternatively, the circuit rigid frame may be made of a stronger material (e.g. titanium) to add additional durability to the body. The small frame may be 3-D printed as two halves and annealed together around the circuit in a similar manner as a clam shell. Alternatively, the frame could be a rigid structure to which the circuit is otherwise attached (e.g., fastened to). In one variation, a protective casing is molded around the rigid frame. In either variation, the method may include integrating an electrode protruding from the rigid frame and/or protective casing. The protruding electrodes are preferably secured to have at least one exposed electrode surface after building the implant body around the circuit (e.g., overmolding a PEEK implant body or closing multipart structure around a PCB). In preferred variations, a portion of the protruding electrode is positioned such that the electrode is fixed in place after the overmolding process.

In a second variation, building an implant body around the circuit S120, includes producing the implant body in at least two complimentary sections with a defined cavity, inserting the circuit into the defined cavity, and attaching the at least two sections of the implant body together. Building an implant body around the circuit in a second variation, functions to create the implant body with an embedded circuit with the additional benefits of enabling shaping of the circuit (e.g. folding and/or bending of a PCB, looping antenna coil) and not exposing the circuit to high temperatures of overmolding.

Producing the implant body in at least two sections includes manufacturing at least two parts of the implant body. Producing the implant body in sections functions to enable insertion of the circuit within implant body from the interior. Producing the implant body may include injection molding, machining, 3D printing, and/or creating using any suitable technique. Producing the implant body in subsections includes producing each subsection of the implant body with a defined cavity, of appropriate size and shape, to house the circuit; wherein, once all subsections are combined, the cavity would match how the circuit would be embedded within the implant body. The defined cavity may be the exact same shape as the circuit or may include curved paths that would match how the circuit should be conformed to fit the cavity.

In simpler implementations (e.g. for a PCB geometry that is not very complex), producing the implant body in at least two subsections preferably includes producing the implant body in exactly two subsections. For complex PCB geometries, wherein the PCB cannot be inserted just between two subsections, multiple implant body subsections may be produced to enable the PCB to be fit. Inserting the PCB, functions in embedding the PCB within the defined PCB cavity, thereby combining each subsection to form the implant body. Inserting the PCB may include bending segments of the PCB sufficiently to fit into cavity.

Once the circuit is properly inserted into the cavity, each body implant section is preferably attached together. Attaching can include annealing, fixturing (e.g., fastening with screws or clamp), or otherwise fixing together. Attaching each section of the implant body together functions to form a complete implant body construct with an embedded circuit. Attaching each section of the implant body together may be accomplished by epoxy glue, sonic welding, or through any other process that is non-toxic and very long lasting.

In a third variation of Block S120, the first and second variation of building an implant body around the circuit are combined. The second variation may be implemented in the building a small frame for the circuit. Once embedded, the small frame and circuit may then be overmolded.

As shown in FIG. 27, a second method variation for manufacturing a medical implant device with an at least partially embedded circuit includes obtaining a circuit S210, obtaining an implant body S220, manufacturing a defined circuit cavity in the implant body S230, and embedding the circuit within the implant body S240. The second method functions in creating a medical implant device after fabrication of the implant body. In variations that include a casing, the method further includes integrating the casing with the implant body. In some variations, the method may be implemented for each implant subcomponent separately, prior to combining them to form the implant body. In these variations, the method may comprise: for each implant body subcomponent, obtaining a circuit; obtaining an implant body subcomponent, manufacturing a defined circuit cavity in the implant body subcomponent; embedding the circuit within the implant body subcomponent. and integrating all implant body subcomponents.

Block S210, which includes constructing a circuit, functions substantially identical to constructing a circuit S110 as described above. Dependent on the variation, the circuit may comprise an integrated circuit (IC), an application specific integrated circuit (ASIC), a printed circuit board (PCB), and/or any type of circuitry or associated electronic components. In variations/steps that include bending and/or modifying the shape, the circuit preferably comprises a planar/board-like structure (e.g. PCB).

Block S220, which includes obtaining an implant body, functions to get a desired implant body. Obtaining an implant body S220 may include obtaining an implant body of any desired size or shape as desired for implementation. In a method of preferred embodiment, obtaining an implant body S220 includes obtaining a spinal cage of a specific type for desired implementation. Obtaining an implant body S220 may include either building the implant body or otherwise making use or configuring a produced implant body. Building an implant body may include forming an implant body through a variety of manufacturing processes such as injection molding, 3D printing, machining, and the like. At least an external portion of the implant body is preferably comprised of biologically compliant material such as PEEK.

Block S230, which includes manufacturing a defined circuit cavity in the implant body, functions to create a cavity within the implant body for placement of the circuit. In one variation, manufacturing a defined circuit cavity S230, includes performing subtractive machining and thereby cutting a slit, groove, or opening to house the circuit. The shape, path, profile, and other features of the defined circuit cavity is discussed above and may be manufactured into the implant body. Milling, drilling, application of a water jet or laser cutter, or any suitable technique for subtractive manufacturing may be used. Alternatively, the implant body in block S230 may incorporate manufacturing a defined circuit cavity. For example, the implant body could be molded to include a defined circuit cavity. In another variation, the implant body may be a multipart design and each part could be manufactured separately and when attached cooperatively create a defined circuit cavity.

Block S240, which includes embedding the circuit within the implant body functions in creating an implant body construct with an embedded circuit. Embedding the circuit within the implant body S240 includes positioning and shaping the circuit such that it fits within the cavity. For PCB variations, this may include bending/folding and placing the PCB within the implant body. Embedding the circuit may additionally include covering the surface of the PCB with a protective material. The protective material may be any non-toxic, non-reactive material (e.g. silicone, resin) that protects the circuit from the external environment while implanted in a living body. Other techniques for sealing or enclosing the circuit may alternatively be used. In some variations, embedding the circuit within the implant body S240 may include printing the circuit and/or printing circuit components onto, or into, the implant body.

For either method that includes a system with a casing, and/or for method implementations that comprise initially creating implant body subcomponents, as shown in FIGS. 28-31, the method further includes integrating the implant body subcomponents (e.g. integrating the casing with the implant body). Integrating the implant body subcomponents, functions to produce a single "implant body" from the casing and an implant body subcomponents, thereby producing a single medical implant device.

For the casing, integrating the casing with the implant body may comprise fixing, adhering, attaching, incorporating, and or integrating the casing with the implant body in another desired manner. In preferred variations, integrating the casing with the implant body comprises irreversibly joining the implant body and the casing. Preferably, the implant body and the casing are sealed together. As shown in FIG. 31, integrating the casing with the implant body may comprise laser welding the casing to connector piece of the implant body. Laser welding the casing may hermetically seal the case and irreversibly join it to the implant body.

Dependent on the implementation, the implant body and the casing may be constructed simultaneously, or separately. Additionally, if the two components are constructed separately, one may be produced prior to the other. In some of these variations, integrating the casing with the implant body may occur concurrent to the production of the second component. For example, a first component may be initially produced, and the second component may be produced and integrated simultaneously onto the first component.

In a first variation, the casing may be produced in a separate process than the implant body. Integrating the casing with the implant body may then comprise joining/attaching/adhering the two geometries once each has been produced in separate processes.

In a second variation, the casing or the implant body is produced first. In a first example, wherein the casing is produced first, integrating the casing with the implant body may comprise overmolding the implant body onto the casing. In a second example, wherein the implant body is produced first, integrating the casing with the implant body may comprise 3D printing the casing onto the implant body.

Additionally, both methods may further include steps required in making the medical implant device functional. For a preferred variation of a spinal cage implant, additional steps may include inserting external electrode components, inserting wiring through the electrode, connecting to external devices, and any other required or desired steps to make the spinal cage functioning as desired. Electrodes may also be directly printed on the PCB substrate and/or implant body for example by depositing titanium or platinum or any other suitable electrode material onto the PCB substrate to form an electrode 132 of the appropriate size and/or form. For electrodes printed on a PCB, this is preferably done during the manufacturing of the PCB but may also be done as a separate step; for example, by depositing metal at appropriate sections of a PCB that has already been manufactured to house other system components but not electrodes. Alternatively, electrode sites can be formed by depositing suitable electrode metals such as platinum and/or titanium onto exposed metal shapes formed as part of manufacturing a PCB that prior to this step contained no areas of exposed platinum or titanium.

Figure 29:
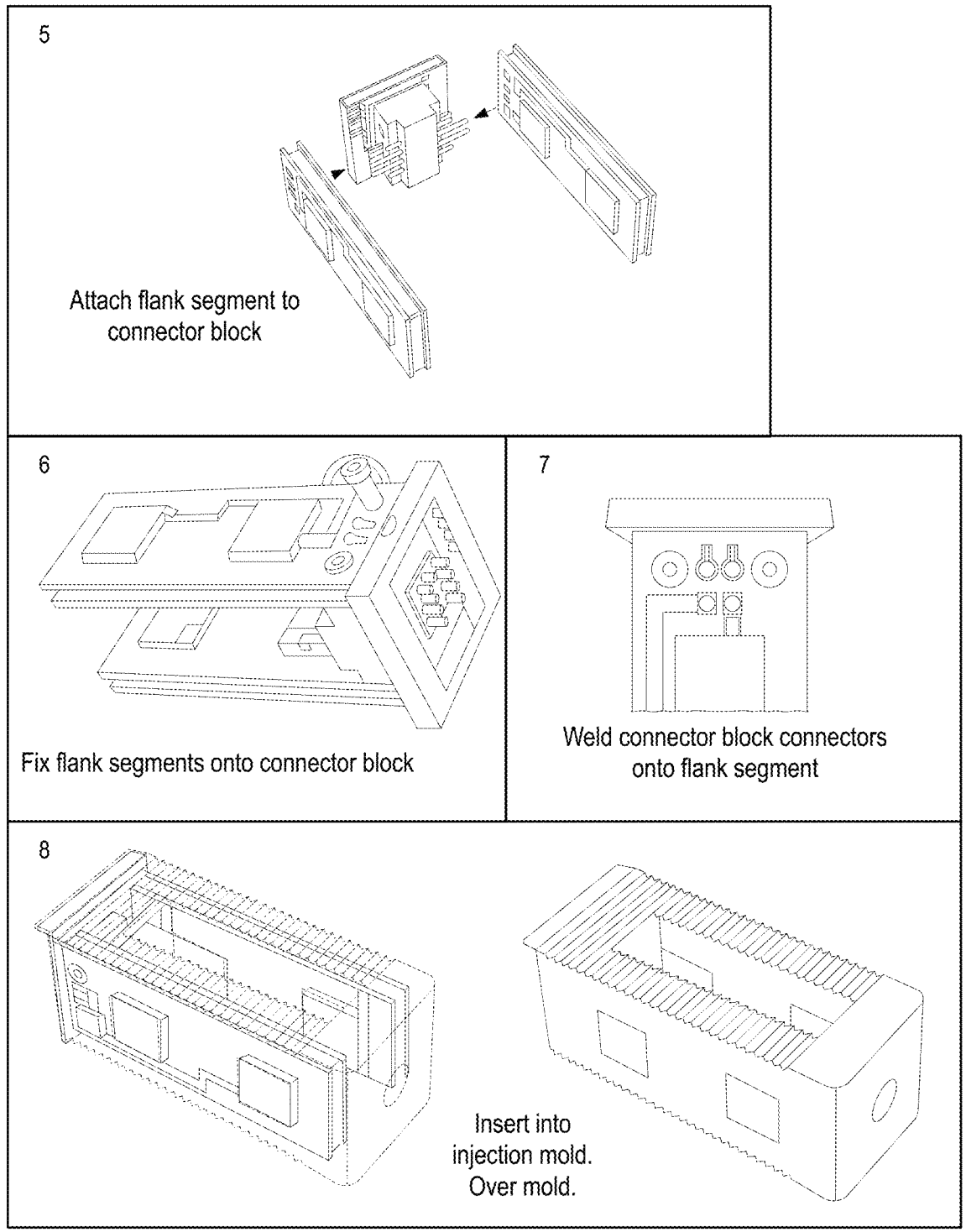

Either method may be implemented in multiple ways, wherein sections of the implant body construct may be manufactured separately or together. In one example, the first method may be implemented to produce the implant body in sections, as shown in FIG. 28, which may then be combined to form the implant body, as shown in FIG. 29. The casing may be manufactured separately, as shown in FIG. 30, which can then be attached to the implant body (e.g. by welding), as shown in FIG. 30.

Figure 30:
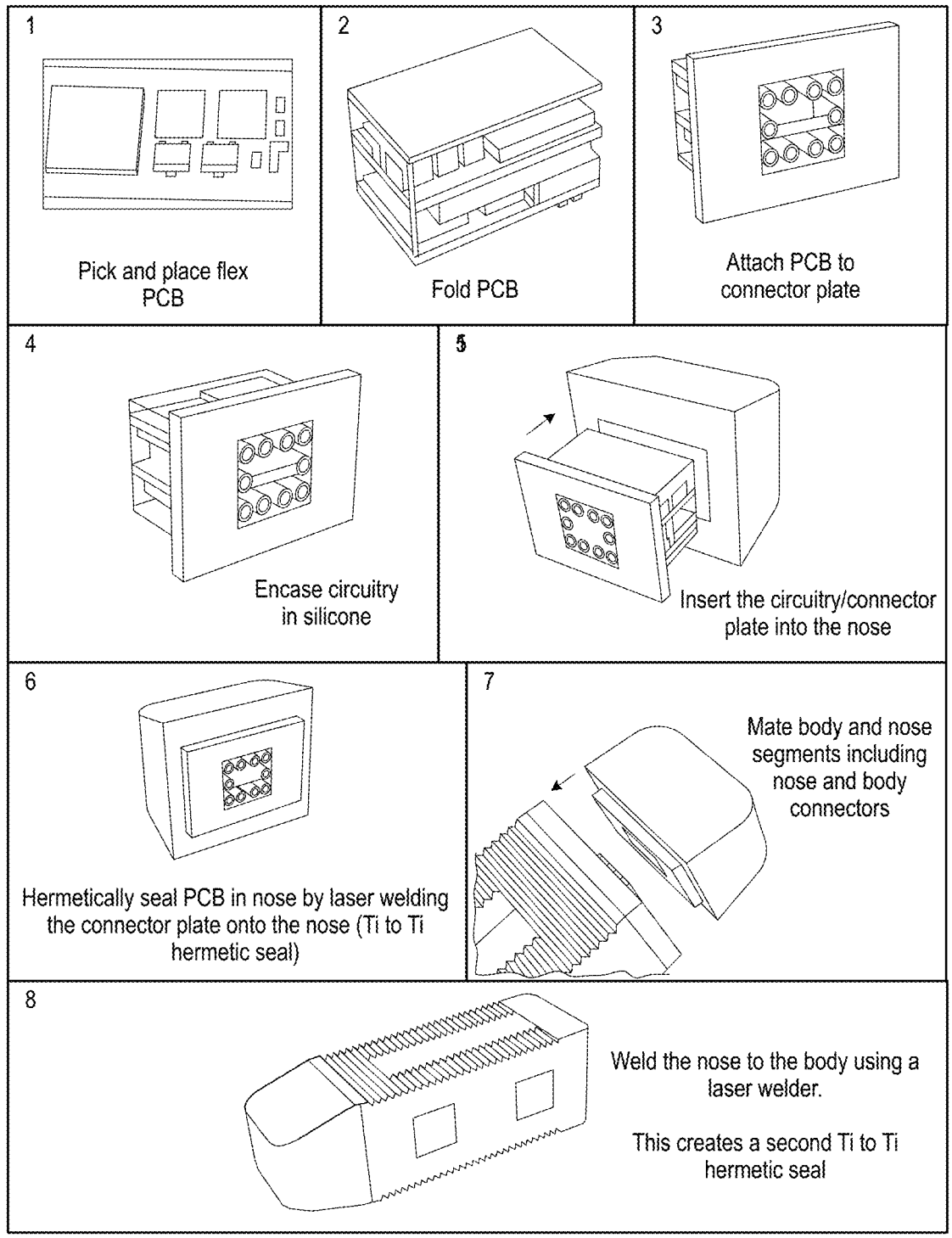
FIG. 30 is a stepwise example illustration of a method implementation.

One example implementation of the method for the construction of a TILF cage with a casing is demonstrated in FIGS. 28-30. As shown in FIGS. 28 and 30, a circuit is obtained for the implant body (e.g. circuitry surface for the antenna and electrodes) and the casing (e.g. a flexible PCB that is then folded to the appropriate configuration). As shown in FIG. 28, the sides of the implant body (e.g. flank segments and connector blocks) are then constructed by an injection molding process (e.g. using PEEK), and electrodes are attached or patterned within the flank segments, the antenna is wrapped around the flank, and wiring is used to connect these segments. In this implementation the antenna is additionally embedded in silicone.

As shown in FIG. 29, the flank segments are then connected, both physically and electrically, to the connector block and then welded into place. Screws or other fixture mechanisms may be used to further attach the flank segments to the connector block. The "completed" body is then inserted into an injection mold and overmolded to form a single piece implant body. with a connector piece to connect to the casing.

The body of the casing may be pre-made or molded to the desired specifications to match the size of the implant body and able to fit the PCB. As shown in FIG. 30, the folded PCB component can be connected to a casing connector plate and then encased in silicone, which may protect the PCB. The encased PCB component is then inserted into the casing, such that the PCB is within the casing and the connected connector plate is on the exposed opening of the casing. The PCB may then be hermetically sealed within the casing (e.g. by laser welding the connector plate to the casing). The casing may then be integrated with the implant body by combining the connector components of the casing and the implant body. In some implementations, the casing and the implant body may be hermetically sealed together (e.g. by laser welding). In some variations, the implant body and casing are welded together at an angle going inwards from the circumference of the implant body, such that pressure and forces exerted on the faces of the implant body 100 are not directly applied to the casing and the connection of the casing and the implant body (FIG. 30).

As a person skilled in the art will recognize from the previous detailed description and from the figures and claims, modifications and changes can be made to the embodiments of the invention without departing from the scope of this invention as defined in the following claims.

We claim:

1. A system for embedded electronics within a medical spinal cage implant comprising:
    an implant body made of polyether ether ketone (PEEK) material;
    a circuitry system comprising:
        a circuitry surface that is at least partially embedded along a path within a defined internal cavity of the implant body, wherein the circuitry surface comprises a set of electrical components made of biocompatible materials that is integrated with the circuitry surface, the set of electrical components comprising a set of electrodes and an antenna, wherein the implant body is formed around the circuitry surface, and
        a casing circuitry subsystem comprising non-biocompatible circuit components;
        a casing that is a sealed metal structure directly connected to the implant body, wherein the casing circuitry subsystem is enclosed within the casing, and the casing comprising exposed electrical connectors that operatively couple the casing circuitry subsystem and the set of electrical components of the circuitry surface.

2. The system of claim 1, wherein the casing circuitry subsystem comprises a printed circuit board (PCB) contained within the casing; and further comprising wiring that electrically connects the PCB and the set of electrical components embedded within the implant body.

3. The system of claim 1, wherein the circuitry surface comprises a printed circuit board (PCB).

4. The system of claim 3, further comprising a sheathing with a protective structure, wherein the at least partially embedded portion of the circuitry surface is enclosed within the sheathing.

5. The system of claim 4, wherein the sheathing is composed of silicone, such that the PCB embedded in the defined cavity is enclosed and covered by a silicone sheathing.

6. The system of claim 3, wherein the path comprises a single straight line, or curved, path, and the PCB is embedded within the implant body along the single straight line, or curved, path.

7. The system of claim 3, wherein the path comprises multiple straight lines or curved, paths, and the embedded PCB along the multiple paths comprises a folded PCB, roughly matching the shape of the multiple paths.

8. The system of claim 7, wherein the folded PCB is in a table geometry, such that so that the middle portion of the PCB has a face normal to the direction of insertion into the implant body, and that both ends of the PCB are bent and inserted into a deeper portion of the defined PCB cavity.

9. The system of claim 7, wherein the folded PCB may be folded such that the PCB has at least one normal surface to all three space dimensions.

10. The system of claim 9, wherein each normal surface of the PCB contains an antenna component such that the antenna spans all space dimensions.

11. The system of claim 7, wherein the folded PCB is folded in an accordion manner, such that the PCB is folded back and on itself multiple times.

12. The system of claim 11, wherein the antenna comprises multi-layered geometry, wherein adjacent layers of the PCB contain a part of the antenna, thus forming a relatively three-dimensional antenna comprising stacked planar folds.

13. The system of claim 1, wherein the implant body is a molded thermoplastic, and wherein the casing is hermetically sealed and laser welded to the implant body, and the circuitry system enclosed in the casing comprises a PCB that is electrically connected to electronic components within the implant body.

14. The system of claim 1, wherein the implant body comprises a relatively rectangular spinal cage and the casing is physically connected to a shorter lateral side of the spinal cage.

15. The system of claim 14, wherein the circuitry surface comprises two planar surfaces embedded in paths along two longer lateral sides of the rectangular spinal cage; wherein each planar surface contains two electrodes exposed on the exterior surface of the implant body, extending normal and outward from the planar surface; wherein each planar surface contains two electrodes exposed on the interior surface of the implant body, extending normal and inward from the planar surface; and wherein each planar surface has an antenna wrapped around the exterior circumference of the planar surface along the same dimension of the planar surface.

* * * * *